(12) United States Patent
Michael et al.

(10) Patent No.: US 7,230,117 B2
(45) Date of Patent: Jun. 12, 2007

(54) STABLE CYANINE DYE PHOSPHORAMIDITES

(75) Inventors: Maged A. Michael, Placentia, CA (US); Firdous Farooqui, Brea, CA (US); Meda Parameswara Reddy, Brea, CA (US); Hong Li, Irvine, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 357 days.

(21) Appl. No.: 10/889,821

(22) Filed: Jul. 12, 2004

(65) Prior Publication Data

US 2006/0009624 A1   Jan. 12, 2006

(51) Int. Cl.
*C09B 23/00* (2006.01)
*G01N 33/58* (2006.01)

(52) U.S. Cl. ............................ 548/414; 435/6; 530/802
(58) Field of Classification Search ................ 548/414; 435/6; 530/802
See application file for complete search history.

(56) References Cited

U.S. PATENT DOCUMENTS

| 5,556,959 | A  | 9/1996  | Brush et al. |
| 5,571,388 | A  | 11/1996 | Patonay et al. |
| 6,027,709 | A  | 2/2000  | Little et al. |
| 6,110,630 | A  | 8/2000  | Reddy et al. ................. 430/93 |
| 6,331,632 | B1 | 12/2001 | Reedy et al. |
| 6,335,450 | B1 | 1/2002  | Farooqui et al. |
| 6,593,148 | B1 | 7/2003  | Narayanan |
| 6,716,994 | B1 | 4/2004  | Menchen et al. |

FOREIGN PATENT DOCUMENTS

| EP | 0 753 584 A1 | 1/1997 |
| EP | 0 670374 B1  | 5/1998 |

OTHER PUBLICATIONS

Narayanan et al., "New Year Infrared Dyes for Applications in Bioanalytical Methods", Proceedings of SPIE, 2388, 6-15, 1995.*

Narayanan, et al; A New Method for the Synthesis of Heptamethine Cyanine Dyes: Synthesis of New Near-Infrared Fluorescent Labels; J.Org Chem. 1995, 60, 2391-2395.

G.A. Reynolds, et al.; Stable Heptamethine Pyrylium Dyes That Absorb in the Infrared; J. Org. Chem., 1997, 42(5), 885-888.

Strekowski, et al; Facile Derivatizations of Heptamethine Cyanine Dyes, Synthetic Communications (1992) 22(17), 2593-2598.

Strekowski, et al.; Functionalization of Near-Infrared Cyanine Dyes; J. Heterocyclic Chem., 33, 1685-1688, 1996.

Strekowski et al.; Substitution Reactions of a Nucleofugal Group on Heptamethine Cyanine Dyes, J. Org. Chem., 1992, 57(17), 4578-4580.

International Search Report, Jan. 13, 2006.

* cited by examiner

*Primary Examiner*—Fiona T. Powers
(74) *Attorney, Agent, or Firm*—Hogan & Hartson LLP

(57) ABSTRACT

This invention provides dye phosphoramidites, particularly phosphoramidites of substituted cyclic bridged cyanine and related dyes, of the general formula:

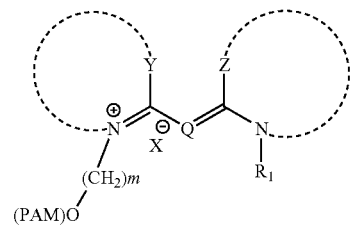

In this formula, each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; (PAM) is a phosphoramidite group; X is a negative ion; and Q is L-W, wherein L is a conjugated cyclic moiety and W is $OR_2$, wherein $R_2$ is a second alkyl. Methods of making and using the dye phosphoramidites are also provided.

37 Claims, 15 Drawing Sheets

Fig. 3
Step 1. Synthesis of Cyclic-Cy7(Cl)-OH:
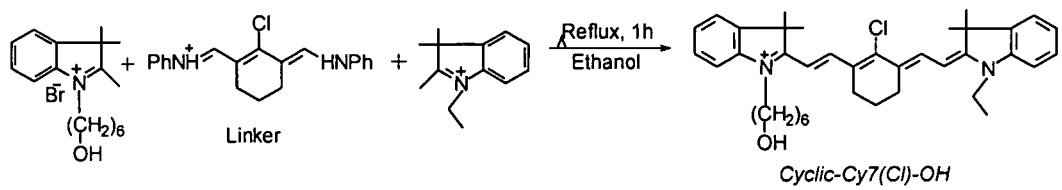
*Cyclic-Cy7(Cl)-OH*
Step 2. Synthesis of Cyclic-Cy7(OMe)-OH:
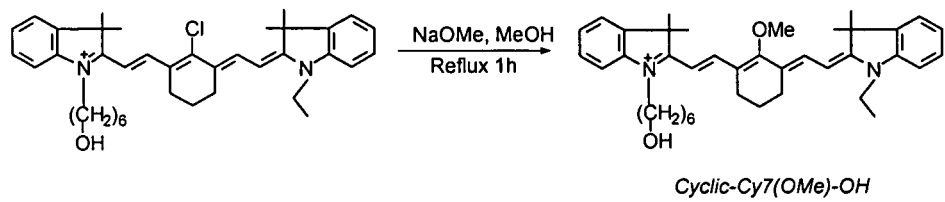
*Cyclic-Cy7(OMe)-OH*
Step 3. Synthesis of Cyclic-Cy7(OMe)-phosphoramidite:
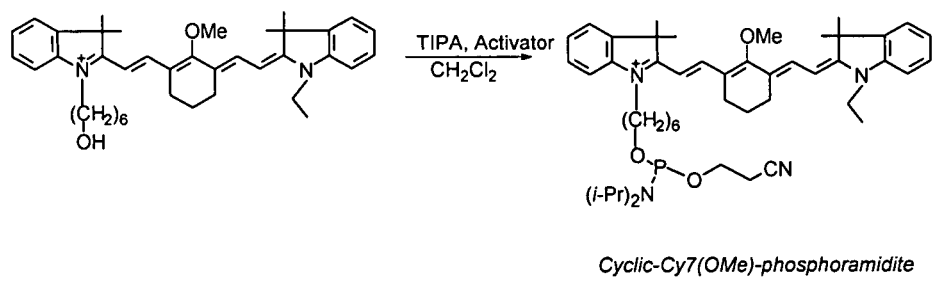
*Cyclic-Cy7(OMe)-phosphoramidite*
Activator: Example 3, Ethylthiotetrazole 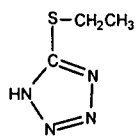
Example 4: Diisopropylammonium tetrazolide (DIIPT) 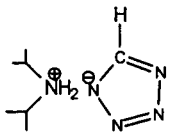

Fig. 9

Table 1
Stability Study at Room Temperature

Cyclic-Cy7(OMe) phosphoramidite

| Time at Room Temp(~25°C) | Purity by HPLC | Abs. Max. | Emis. Max. | $^{31}$P NMR | Coupling Efficiency to Oligonucleotide |
|---|---|---|---|---|---|
| 0 Time | 81.94% | 754 nm | 782 nm | 66.46% | 46% |
| 1 week | N/A | 754 nm | 782 nm | 61.81% | N/A |
| 3 weeks | N/A | 754 nm | 782 nm | 52.25% | N/A |
| 4 weeks | 68.92% | 754 nm | 782 nm | 50.81% | 35.49% |

Cyclic-Cy7(H) phosphoramidite

| Time at Room Temp(~25°C) | Purity by HPLC | Abs. Max. | Emis. Max. | $^{31}$P NMR | Coupling Efficiency to Oligonucleotide |
|---|---|---|---|---|---|
| 0 Time | 67.60% | 748 nm | 782 nm | 70.06% | 44.83% |
| 1 week | N/A | 748 nm | 782 nm | 62.77% | N/A |
| 3 weeks | N/A | 748 nm | 782 nm | 53.81% | N/A |
| 4 weeks | 52.11% | 748 nm | 782 nm | 51.15% | 15% |

4 weeks at room temperature is equal to 13 months at 4°C.
$^{31}$P NMR scale is in ppm (parts per million). The percentage refers to the integration of the main peak at 144.64 ppm.
Coupling efficiency is measured by coupling the phosphoramidite to an oligonucleotide. The oligonucleotide is synthesized and then coupled to the phosphoramidite, cleaved and de-protected with mild de-protection reagent and analyzed on reverse phase HPLC. The percentage is area percentage of the labeled oligonucleotide on HPLC.

Fig. 10

Stability Study of Cyclic-Cy7(OMe) Phosphoramidite vs. Cyclic-Cy7(H) Phosphoramidite at 37°C

Table 2

Cyclic-Cy7 (OMe) phosphoramidite

| Time at 37°C | Purity by HPLC | Em. (780nm)/Abs. (755nm) ratio | $^{31}$P NMR | Coupling efficiency to Oligonucleotide |
|---|---|---|---|---|
| 0 Time | 61.65%, | 738/0.6098=1210 | 100% | 43% |
| 3 Days | 66.07%, | 697/0.7054=988 | 80% | 45% |
| 5 Days | 65.38%, | 729/0.6865 = 1062 | 84% | 37.42% |
| 7 Days | 56.95%, | 710/0.6525=1088 | 85% | 17% |

Table 3

Cyclic-Cy7 (H) phosphoramidite

| Time at 37°C | Purity by HPLC | Em. (778nm)/Abs. (748 nm) ratio | $^{31}$P NMR | Coupling efficiency to Oligonucleotide |
|---|---|---|---|---|
| 0 Time | 43.93% | 923/0.4903=1882 | 80% | 30% |
| 3 Days | 35.24% | 862/0.5903=1460 | 57% | 26% |
| 5 Days | 23.88% | 836/0.5055 = 1653 | 48% | 2% |
| 7 Days | 20.92% | 753/0.5813=1295 | 40% | 0% |

Fig. 13

Table 4

| Estimated Half-Life at Room Temperature (Weeks) | | | | | | | |
|---|---|---|---|---|---|---|---|
| Oligo 1 | | Oligo 2 | | Oligo 3 | | Average | |
| Cyclic-Cy7 (H) | Cyclic-Cy7 (OMe)* | Cyclic-Cy7 (H) | Cyclic-Cy7 (OMe) | Cyclic-Cy7 (H) | Cyclic-Cy7 (OMe) | Cyclic-Cy7 (H) | Cyclic-Cy7 (OMe)* |
| 0.9 | 17.67 | 1.4 | 5.2 | 1.8 | 2.1 | 1.3 | 3.7 |

Half-life estimated from nonlinear curve-fit (one phase exponential decay) of data.
* Oligo 1 Cyclic-Cy7(OMe) half-life excluded from average calculation due to it's anomalously high estimated value.

Fig. 15
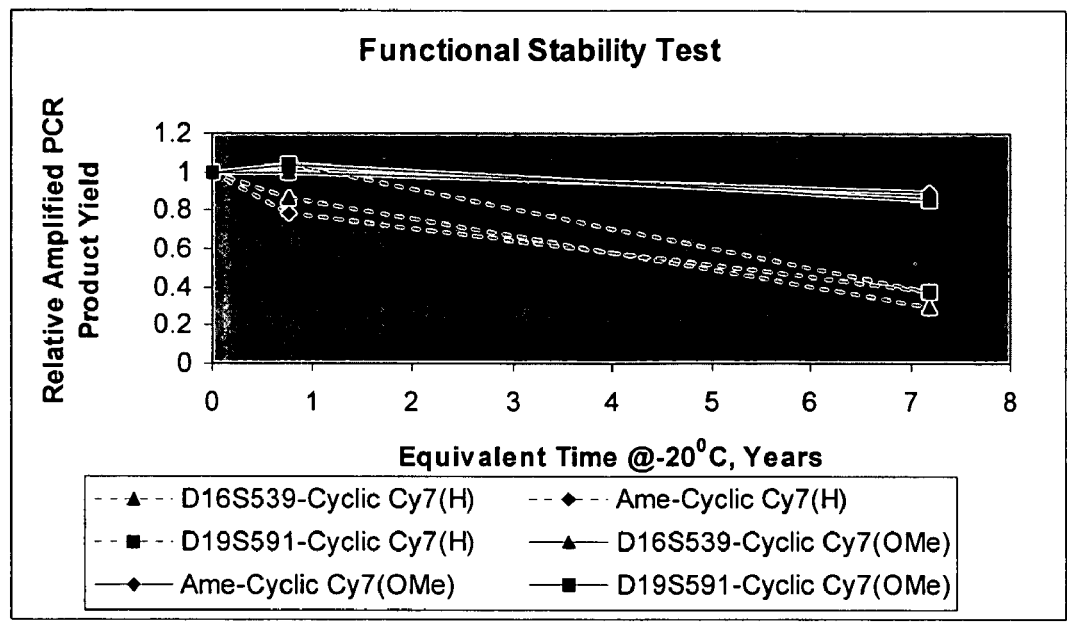
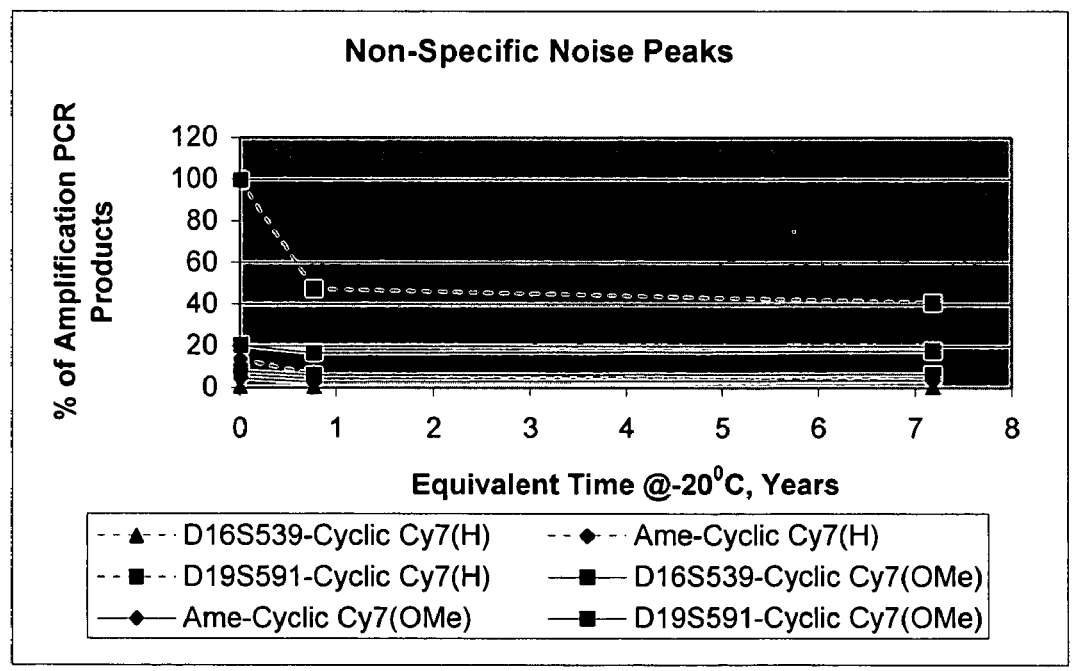

SEQUENCE LISTING

<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
gatcccaagc tcttcctctt                                               20

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
ccctgggctc tgtaaagaat agtg                                          24

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
ttccagccta ggtagcagtg                                               20

STABLE CYANINE DYE PHOSPHORAMIDITES

BACKGROUND OF THE INVENTION

1. Area of the Art

The invention relates generally to cyanine dyes and specifically to stabilized cyclic-bridged cyanine dye phosphoramidites, their synthesis and methods of their use in labeling of biomolecules.

2. Description of the Prior Art

Many procedures employed in biomedical research and recombinant DNA technology rely heavily on the use of oligonucleotides as probes, primers, linkers, adapters, and gene fragments. Several of these uses are described in common laboratory manuals, such as Molecular Cloning, A Laboratory Manual, Second Ed., J. Sambrook, et al., Eds., Cold Spring Harbor Laboratory Press, 1989; and Current Protocols In Molecular Biology, F. M. Ausubel, et al., Eds., Current Publications, 1993. Many applications, such as automated DNA sequencing and mapping, in situ detection of hybridization, detection of PCR products, and structural studies, require labeled oligonucleotides. While radioactive labels were traditionally used in these applications, recently certain cyanine dyes have proved to be quite useful in the labeling of biomolecules.

Cyanine dyes offer many desirable properties, including safe handling, absorbency at longer wavelengths, high extinction coefficient, relatively high quantum efficiency, small molecular size, ease of chemical manipulation, and reasonable stability to reagents, pH and temperature. Because of a low background fluorescence of biological materials and a high absorbency of cyanine dyes in the longer wavelength portion of the spectrum, cyanine dyes provide excellent signal-to-noise ratios. By modifying the chromophore portion of cyanine dyes, different fluorescent labeling reagents absorbing and emitting in a broad spectrum range from 400 to nearly 1100 nm can be obtained. The versatility of functional groups that can be incorporated into cyanine dyes permits control over the solubility of the dye and labeled product, and helps reduce non-specific binding of the labeled materials to irrelevant components in an assay mixture (U.S. Pat. Nos. 5,569,587 and 5,627,027).

At present, labeling of oligonucleotides with cyanine dyes is performed by a manual, two-step procedure. First, an oligonucleotide is synthesized and, then, an activated cyanine dye is linked to the 5' end of the synthesized oligonucleotide. Usually, cyanine dyes are activated by an introduction of reactive groups that assist in covalent attachment of cyanine dyes to oligonucleotides (see, for example, U.S. Pat. Nos. 5,569,587 and 5,627,027). This two-step method is slow (4-5 days), tedious, expensive, and often produces undesirable organic by-products. In an alternative, more convenient, one-step approach, a fluorescent dye is converted into a phosphoramidite and is used in direct labeling of an oligonucleotide during its synthesis. However, currently available phosphoramidites of cyanine dyes are substantially more expensive and less stable than their standard, unmodified counterparts.

U.S. Pat. No. 5,556,959 ('959) discloses the use of carbocyanine phosphoramidites to label synthetic oligonucleotides. The cyanine phosphoramidites of the '959 patent, however, contain protecting groups, such as trityl; 4-O-monomethoxytrityl; 4,4'-O-dimethoxytrityl or acyl. Protecting groups are usually associated with instability during storage and handling, thus making these phosphoramidites less valuable commercially.

U.S. Pat. No. 6,331,632 ('632) discloses the use of cyanine phosphoramidite dyes for labeling synthetic oligonucleotides. The dyes of the '632 patent are commercially useful, however they are still somewhat costly and are characterized by some instability.

U.S. Pat. No. 6,716,994 ('994) discloses a class of cyanine dyes that are modified at one of the hetercyclic ring nitrogen atoms with a mobility-modifying moiety. The '994 patent recognizes inherent instability of cyanine dyes and suggests protecting exocyclic amines and other functionalities with removable base-labile protecting groups.

SUMMARY OF THE INVENTION

In view of deficiencies of the related art, it is an object of the present invention to provide highly stable and cost effective cyanine dye phosphoramidites for direct labeling of biomolecules. It is also an object of the present invention to provide convenient methods for synthesizing phosphoramidites that do not require steps of introduction and removal of protecting groups. It is a further object of the present invention to provide a method for labeling an oligonucleotide directly during its synthesis.

These and other objects are achieved in dyes of the present invention having the following general formula (I):

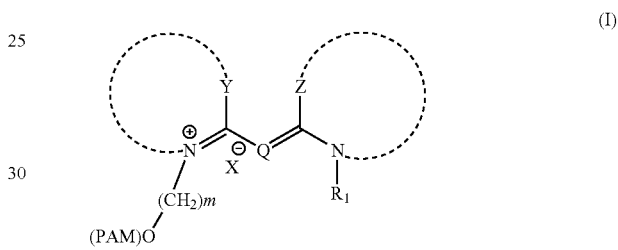

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; (PAM) is a phosphoramidite group; $X^{\ominus}$ is a negative ion; and Q is L-W, wherein L is a conjugated cyclic moiety and W is $OR_2$, wherein $R_2$ is a second alkyl.

According to one embodiment of the present invention, the dye is a cyanine dye selected from the group consisting of cyclic tricarbocyanine dye (cyclic Cy7), benzoindole cyclic cyanine dye (cyclic BCy7), and dibenzoindole cyclic cyanine dye (cyclic DBCy7). The phosphoramidite group may be a N,N-diisopropyl-O-β-cyanoethyl phosphoramidite group.

Another aspect of the present invention provides a method of synthesizing a dye phosphoramidite. The method includes the steps of:

(a) forming a hydroxy derivative of the dye having a formula (II):

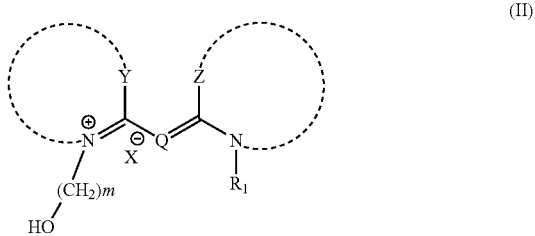

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; $X^\ominus$ is a negative ion; and Q is L-W, wherein L is a conjugated cyclic moiety and W is $OR_2$, wherein $R_2$ is a second alkyl; and (b) replacing hydrogen of the OH group of the hydroxy derivative (II) with a phosphoramidite group.

In one embodiment of the present invention, the step of synthesizing the hydroxy derivative of the dye having the formula (II) comprises reacting compounds (XI), (XII) and (XIII) under conditions that allow formation of a chlorine derivative of the dye having a general formula (XIV):

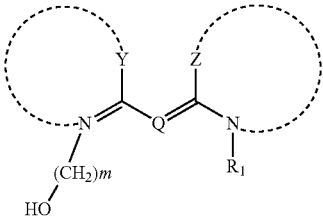

(XIV)

wherein Q is L-Cl, wherein L is a conjugated cyclic moiety and Cl is chlorine;

Compound (XI) may be any compound having a general formula:

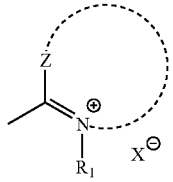

(XI)

Compound (XII) has a formula:

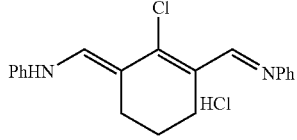

(XII)

wherein Ph is phenyl; and

Compound (XIII) may be any compound having a formula:

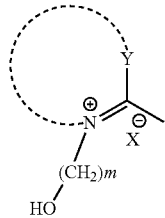

(XIII)

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; and $X^\ominus$ is a negative ion.

In one embodiment of the present invention, the step of synthesizing the hydroxy derivative of the dye further involves refluxing the chloride derivative of cyanine dye (XIV) under conditions that allow the formation of the hydroxy derivative of cyanine dye (II).

A further aspect of the present invention provides a method wherein luminescent dye phosphoramidites of the present invention having the general structural formula (I) are used to label oligonucleotides directly.

The present invention provides both economic and technical advantages over the use of other dyes in the labeling of biomolecules such as oligonucleotides, proteins, and peptides. As explained in detail below, dye phosphoramidites of this invention may be used directly on any DNA synthesizer, for example, oligonucleotide ABI 394 (Beckman Coulter, Calif.), to automatically add the dye to the oligonucleotide during its synthesis. By using dye phosphoramidites with no protecting groups, the total time for the preparation of a labeled oligonucleotide is greatly reduced, since the step of removing a protecting group is eliminated. Furthermore, an incorporation of a cyclic moiety substituted with an $OR_2$ group into the chain of conjugated double bonds of Cy7 and DBCy7 phosphoramidites prevents their partial conversion into Cy5-like species and leads to formation of stable dyes.

The stability of phosphoramidites of the present invention, having a cyclic bridge which is substituted with an $OR_2$ group, greatly exceeds that of phosphoramidites of unsubstituted cyclic bridged dyes such as those described in the '632 patent, which reflects earlier work of the inventors of this application. The substituted cyclic bridge cyanine dye phosphoramidites of the present invention maintain their purity over substantially longer periods of time than the phosphoramidites of the '632 patent. They also show increased oligonucleotide binding efficiency. When used to label oligonucleotides, they demonstrate half lives that are far greater than that of the dye phosphoramidites of the prior art. This means that in addition to cost and time saving provided by utilizing dye phosphoramidites of this invention for labeling of oligonucleotides and other biomolecules, higher over-all yield of labeled product is also achieved as compared to biomolecules labeled with phosphoramidites that are currently available.

The invention is defined in its fullest scope in the appended claims and is described below in its preferred embodiments.

DESCRIPTION OF THE FIGURES

The above-mentioned and other features of the present invention and the manner of obtaining them will become more apparent, and will be best understood, by reference to the following description, taken in conjunction with the accompanying drawings, in which:

FIG. 3 shows a reaction scheme, illustrating synthesis of cyclic ($OCH_3$)-Cy7 phosphoramidite in accordance with another embodiment of the present invention, which is described in Examples 1, 2 and 4;

FIG. 9 shows Table 1, which contains stability data for Cyclic-Cy7(OMe) phosphoramidite and Cyclic-Cy7(H) phosphoramidite at room temperature;

FIG. 10 shows Table 2, which contains stability data for Cyclic-Cy7(OMe) phosphoramidite at 37° C. and Table 3, which contains stability data for Cyclic-Cy7(H) phosphoramidite at 37° C. 3. ³¹P NMR scale is in ppm (parts per million). The percentage refers to the integration of the main peak at 144.64 ppm. Coupling efficiency is measured by coupling the phosphoramidite to an oligonucleotide. The oligonucleotide is synthesized and then coupled to the phosphoramidite, cleaved and deprotected with mild deprotection reagent and analyzed on reverse phase HPLC. The percentage is area percentage of the labeled oligonucleotide on HPLC;

FIG. 13 shows Table 4, which contains estimates of the half lives of oligonucleotides 1-3 labeled with phosphoramidites of cyclic bridged Cy7 dyes which had either substituted or unsubstituted cyclic groups;

FIG. 15 shows a chart which depicts the relative amplified PCR yield as a function of equivalent time at −20° C. for D16S539 (Oligo1), Amelogenin (Oligo 2), and D19S591 (Oligo 3) labeled with phosphoramidites of cyclic bridged Cy7 dyes which had either substituted (Cy7(OMe)) or unsubstituted (Cy7(H)) cyclic groups. FIG. 15 also depicts a chart that shows non-specific noise peaks as a percentage of the amplified PCR products as a function of time for D16S539 (Oligo1), Amelogenin (Oligo 2), and D19S591 (Oligo 3) labeled with phosphoramidites of cyclic bridged Cy7 dyes which had either substituted (Cy7(OMe)) or unsubstituted (Cy7(H)) cyclic groups.

DETAILED DESCRIPTION OF THE INVENTION

Figure 1A:
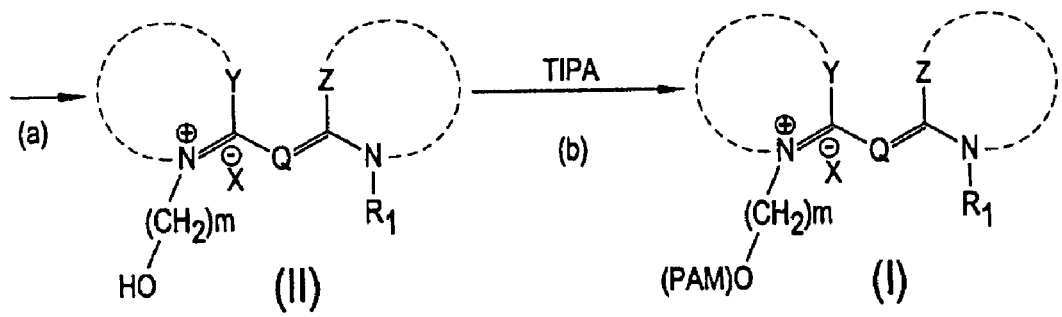
FIGS. 1A and 1B schematically illustrate methods of synthesis of dye phosphoramidites of the present invention.
Figure 1B:
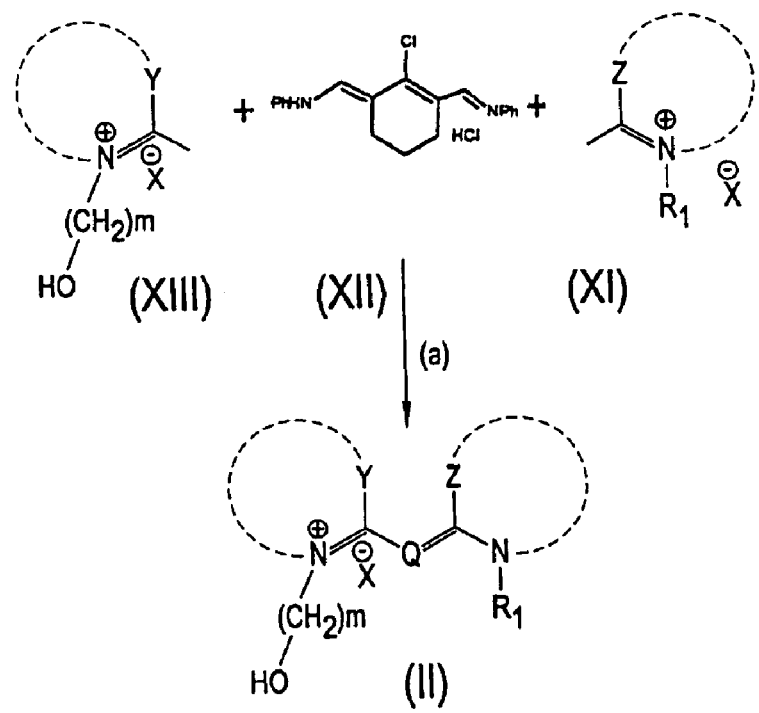

In order to increase stability of phosphoramidites, the present invention utilizes a cyclic bridging group which is substituted with an $OR_2$ group. Accordingly, the present invention provides a dye phosphoramidite, having a formula (I):

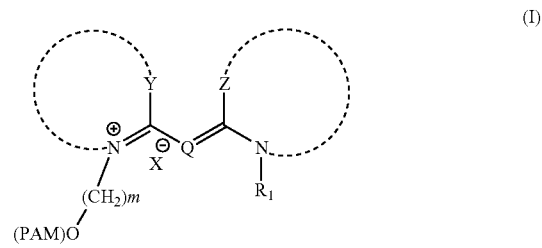

In this formula, each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is a first alkyl; (PAM) is a phosphoramidite group; $X^\ominus$ is a negative ion; and Q is L-W, wherein L is a conjugated cyclic moiety and W is $OR_2$, wherein $R_2$ is a second alkyl.

The activated dyes may contain a heterocyclic ring, a single ring aromatic structure, such as a phenyl ring, or a fused ring structure, such as a naphthyl ring. The aromatic ring may be selected from a group consisting of benzoindolinene, substituted indolinene, and substituted benzoindolinene. The first alkyl group generally possesses one to eighteen carbon atoms. In one embodiment of the invention, the first alkyl group is an ethyl group, containing two carbon atoms. The second alkyl group generally possesses one to eighteen carbons, preferably one to six carbons. In one embodiment of the invention, the second alkyl group is a methyl group, containing one carbon atom. The phosphoramidite group is usually attached to the dye with an alkyl chain. The length of the alkyl chain is 1 to 12 carbon atoms long. In one embodiment, alkyl chain length is about 6 carbon atoms long.

The cyclic moiety L may be conjugated with the surrounding carbon structure. In one embodiment of the present invention, the cyclic moiety is selected from a group consisting of cyclohexene, cyclopentene, and cycloheptene. The Compound (I) of the present invention includes a negative ion $X^\ominus$. Preferably, this ion is a halide, although other negative ions may be used. For example, the negative ion may be $I^\ominus$ or $Br^\ominus$, depending on the synthesis strategy. The phosphoramidite group may be a N,N-diisopropyl-O-β-cyanoethyl phosphoramidite group, although other phosphoramidites known to one skilled in the art may also be used.

Generally speaking, the dyes of the present invention may be any of the fluorescent dyes commonly used for labeling purposes, as long as they incorporate a phosphoramidite group, an alkyl group, and have a cyclic bridge which is substituted with an $OR_2$ group. It is also required that the phosphoramidite group and the first alkyl group are attached to nitrogens in the indole or benzoindole portion of the dye.

The absorption and emission wavelengths of the dye are not restricted to a particular region of the spectrum but may be anywhere from the near UV through the near IR region or beyond these extremes.

According to embodiments of the present invention, the dyes may be cyanine and related dyes. Cyanine dyes have several desirable properties to serve as sensitive detection labels, including absorption at longer wavelengths (which translates into the use of inexpensive detection systems and low background from biological samples at these wavelengths), high extinction coefficient, relatively high quantum efficiency, small molecular size, ease of chemical manipulation without compromising the fluorescence characteristics, and reasonable stability to reagents, pH and temperature.

In one embodiment of this invention, phosphoramidite dyes are selected from the group consisting of cyclic tricarbocyanine dye (cyclic Cy7), benzoindole cyclic cyanine dye (cyclic BCy7), and dibenzoindole cyclic cyanine dye (cyclic DBCy7). The benzoindole cyclic cyanine BCy7 has one benzene group substitution and the dibenzoindole cyclic DBCy7 has two extra benzene group substitutions relative to the corresponding indole cyanine, cyclic Cy7. As such, benzoindole cyclic cyanines have absorption and emission maxima longer than their indole counterparts.

It is a discovery of the present invention that the introduction of an $OR_2$ group into a conjugated cyclic moiety of a dye phosporamidite further increases its stability beyond that of a dye phosphoramidite with an unsubstituted cyclic moiety. The conjugated cyclic group may be selected from a group consisting of cyclohexene, cyclopentene, and cycloheptene. In one embodiment, the cyclic moiety has the following structure (XVa):

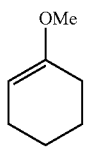

(XVa)

In this embodiment, the cost of synthesis of the resulting phosphoramidite dye is only 60% of the cost of synthesis of the corresponding dye that uses an unsubstituted cyclic moiety.

As discussed in more detail in the Example 5 of the instant invention, phosphoramidites of the present invention surpass phosphoramidites known in the art in their stability. For example, in one embodiment, the phosphoramidites of substituted (Cyclic Cy-7(OMe)) and unsubstituted (Cyclic Cy-7(H)) cyclic cyanine dyes were tested. The phosphoramidite of Cyclic Cy-7(H) was found to be less stable than the phosphoramidite of Cyclic Cy-7(OMe) of the present invention when an accelerated stability study was performed. As measured by HPLC (depicted in FIG. 9, Table 1), the purity of the phosphoramidite of Cyclic Cy-7(H) started at 67.60% and dropped to 52.11% across four weeks at room temperature, while the purity of the phosphoramidite of Cyclic Cy-7(OMe) started much higher at 81.94% and remained high at 68.92% after four weeks at room temperature. In addition, the oligonucleotide coupling efficiency of the phosphoramidite of Cyclic Cy-7(H) dropped from 44.83% to 15% across a four week period at room temperature, while the oligonucleotide coupling efficiency of the phosphoramidite of Cyclic Cy-7(OMe) only dropped from 46.00% to 35.49% across the four weeks at room temperature. (FIG. 9, Table 1). Four weeks at room temperature is equal to thirteen months at 4° C. Thus, this data shows that the phosphoramidite of Cyclic Cy-7(OMe) is much more stable than the phosphoramidite of Cyclic Cy-7(H). The increased purity of the dyes of the present invention and their increased ability to couple with oligonucleotides long after it is produced make them superior to the prior art in their capacity to label oligonucleotides.

Cyclic Cy-7(OMe) phosphoramidite showed the same trend of increased stability over those labeled with Cyclic Cy-7(H) phosphoramidite at 37° C. (FIG. 10, Tables 2 and 3). The purity of the phosphoramidite of Cyclic Cy-7(H) started at 49.93% and dropped to 20.92% across seven days at 37° C., while the purity of the phosphoramidite of Cyclic Cy-7(OMe) started much higher at 61.65% and remained high at 59.95% after seven days at 37° C. In addition, the oligonucleotide coupling efficiency of the phosphoramidite of Cyclic Cy-7(H) dropped from 30% to 0% across a seven day period at 37° C., while the oligonucleotide coupling efficiency of the phosphoramidite of Cyclic Cy-7(OMe) only dropped from 43% to 17% across the seven days at 37° C. The coupling efficiency of the phosphoramidite of Cyclic Cy-7(OMe) held strong at 37.42% by day 5, while the coupling efficiency of the phosphoramidite of Cyclic Cy-7 (H) had already dropped to 2% at day 5. This indicates that the phosphoramidites of the present invention are much more stable than the phosphoramidite of Cyclic Cy-7(H) at 37° C. and are, therefore, more useful for labeling oligonucleotides.

The emission/absorption ratios and the $^{31}P$ NMR data also demonstrate that the phosphoramidite of Cyclic Cy-7(OMe) is more stable than the phosphoramidite of Cyclic Cy-7(H). Changes in the emission/absorption ratio reflect a change in the dye itself. The more ratio changes, the less stable dye is. As can be seen in Table 2, while the phosphoramidite of Cyclic Cy-7(OMe) changed only from a dye ratio of 1210 to 1088 across seven days, Cyclic Cy-7(H) changed from a dye ratio of 1882 to 1295 over the same period of time (Table 3). The $^{31}P$ NMR data reflects purity of the phosphoramidite. The fact that the phosphoramidite of Cyclic Cy-7(OMe) decreased only 15 percentage points as opposed to the 40 percentage point decrease of the phosphoramidite of Cyclic Cy-7(H) across seven days indicates an increased tendency of the phosphoramidite of Cyclic Cy-7(OMe) to remain pure. This data reaffirms that the phosphoramidites of the present invention are much more stable than the phosphoramidite of Cyclic Cy-7(H) at 37° C.

The dye phosphoramidites of the present invention may be used directly on any DNA synthesizer to automatically add the dye to the oligonucleotide. The dye phosphoramidites of this invention do not contain any protecting groups. By the use of dye phosphoramidites with no protecting groups, the total time for the preparation of a labeled oligonucleotide is greatly reduced, since the step of removing a protecting group is eliminated. In addition to cost and time saving provided by utilizing dye phosphoramidites of this invention for labeling of oligonucleotides and other biomolecules, higher over-all yield of labeled product is also achieved as compared to the conventional two-step method.

Another aspect of the present invention provides a method of synthesizing a dye phosphoramidite. The method includes the steps of:

(a) forming a hydroxy derivative of the dye (II), having a formula:

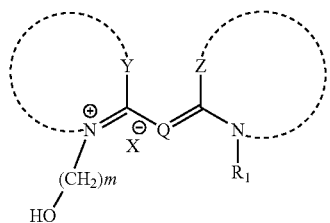

(II)

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; $X^\ominus$ is a negative ion; and Q is L-W, wherein L is a conjugated cyclic moiety and W is $OR_2$, wherein $R_2$ is a second alkyl; and (b) replacing hydrogen of the OH group with a phosphoramidite group.

The hydroxyl derivative (II) may contain a heterocyclic ring, a single ring aromatic structure, such as a phenyl ring, or a fused ring structure, such as a naphthyl ring. In one embodiment, the first and second alkyls are independently selected from a group consisting of alkyls and substituted alkyls having one to eighteen carbons in their backbone. Specifically, in one embodiment, the first alkyl contains two carbons and the second alkyl contains one carbon. Of particular interest are the cyanine dyes discussed above, including cyclic Cy7, cyclic BCy7, and cyclic DBCy7.

In accordance with one embodiment of the present invention, the step (a) of forming a hydroxy derivative of a cyanine dye comprises reacting compounds (XI), (XII) and (XIII) under conditions that allow the formation of a chlorine derivative of the cyanine dye having a general formula (XIV):

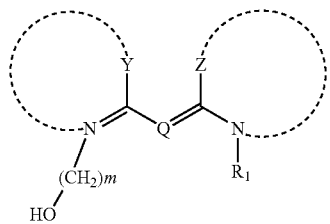

(XIV)

Compound (XI) may be any compound having a general formula:

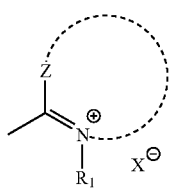

(XI)

Compound (XII) having a formula:

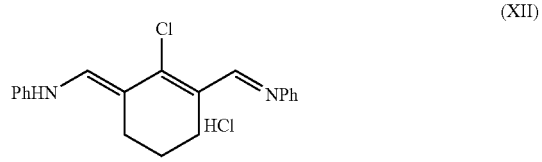

(XII)

wherein Ph is phenyl; and
Compound (XIII) having a formula:

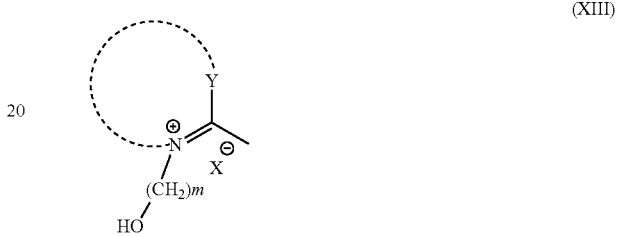

(XIII)

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; and $X^\ominus$ is a negative ion.

The choice of particular Compounds (XI) and (XIII) depends on the type of the dye phosphoramidite to be synthesized. For synthesis of cyclic Cy7 phosphoramidites, one may use Compound (XII) and unsubstituted Compounds (XI) and (XIII), and then substitute the desired $OR_2$ group. Cyclic DBCy7 phosphoramidites may be synthesized by utilizing benz-substituted Compounds (XI) and (XIII) and Compound (XII), and then substituting in the desired $OR_2$ group.

Figure 2:
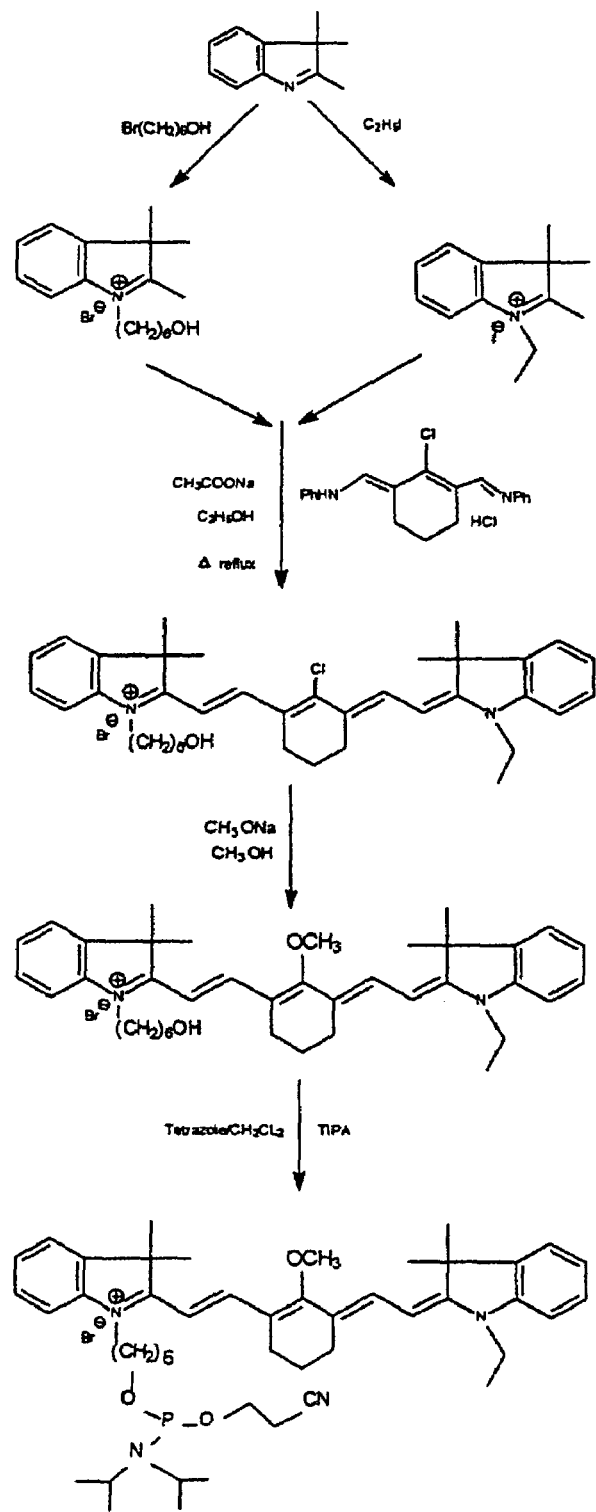
FIG. 2 shows a reaction scheme, illustrating synthesis of cyclic ($OCH_3$)-Cy7 phosphoramidite in accordance with one embodiment of the present invention, which is described in Examples 1, 2 and 3.
Figure 4:
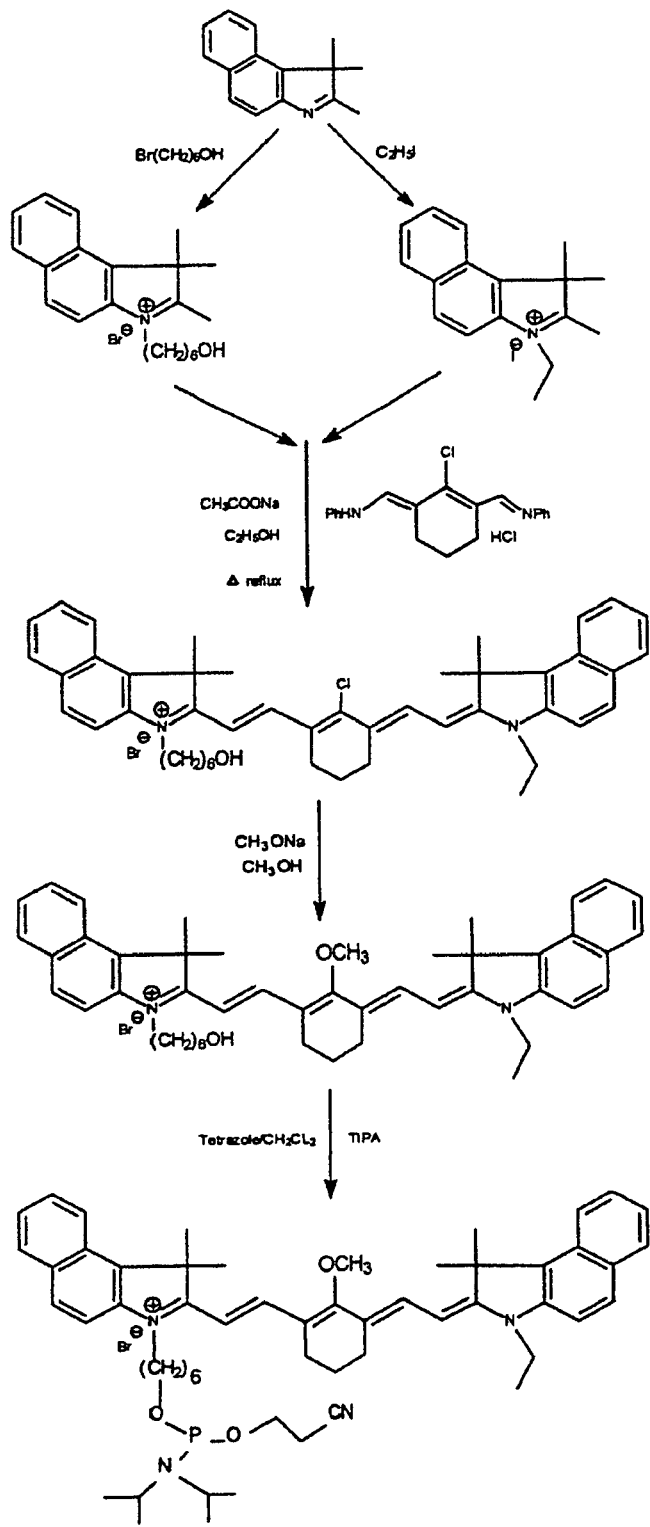
FIG. 4 shows a reaction scheme, illustrating synthesis of cyclic (OCH₃)-DBCy7 phosphoramidite in accordance with further embodiment of the present invention.

One embodiment of the present invention involves synthesis of cyclic Cy7 phosphoramidite (FIG. 2). In this embpodiment, Compound (XI) may be 1-ethyl-2,3,3-trimethylindolinium iodide and Compound (XIII) may be 1-(6-hydroxyhexyl)-1,1,2-trimethylindolinium bromide. In another embodiment, cyclic DBCy7 (FIG. 4) is synthesized. In this embodiment, Compound (XI) may be 1-ethyl-1,1,2-trimethyl-H-Benz(e)indolinium iodide and Compound (XIII) may be 1-(6-hydroxyhexyl)-1,1,2-trimethyl-H-Benz (e)indolinium bromide. Those skilled in the art will appreciate that other phosphoramidites may be synthesized by choosing the appropriate compounds (XI), (XII), and (XIII).

Although any reaction conditions may be used as long as they allow formation of the chlorine derivative (IV), in one embodiment, Compound (XI), Compound (XIII), and anhydrous ethanol are stirred together at room temperature until all solid is dissolved. Compound (XII) is then added to the solution and the solution is stirred again until all solid is dissolved. Sodium acetate anhydrous is then added to the solution, and it is heated to reflux for one hour. The solvent is then removed and the mixture dried under vacuum. The mixture is then dissolved in $CH_2Cl_2$, precipitated in ether, and dried again under vacuum. Once again the mixture is dissolved in $CH_2Cl_2$, and the resulting solution is loaded onto a silica gel column. The column eluted with a graduated solvent containing $CH_2Cl_2$, methanol, acetone, and ethyl acetate, and the product is collected in fractions. The product is then dried overnight at room temperature.

The step of creating the hydroxy derivative of the present invention (II) may further include a step of reacting the chloride derivative of the dye (XIV) with reagents under conditions that allow the formation of the hydroxy derivatitve (II). Although any reaction conditions may be used as long as they allow the formation of the derivative (II), in one embodiment of this invention, the reagent used is $NaOR_2$. $R_2$ may be any alkyl, but in one embodiment a methyl group (Me) is used. In this embodiment, the hydroxy derivative of the OMe cyclic cyanine dye is produced with a general formula (IIa):

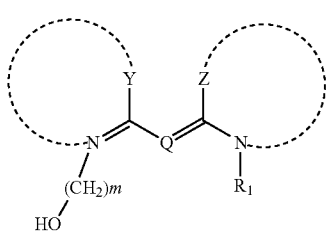

(IIa)

wherein Q is L-OMe, wherein L is a conjugated cyclic moiety.

In one embodiment, NaOMe is mixed with methanol anhydrous in a condenser protected under Argon and stirred until the NaOMe is dissolved completely. Then, the hydroxy and chloride derivative of the dye is mixed into the flask, and the mixture is heated to reflux for 1 hour. The solution is cooled and the solvent is evaporated under vacuum. The residue is then dissolved in $CH_2Cl_2$, and loaded onto a silica gel column. The column is eluted, and the product is collected. The solvent is evaporated under vacuum, and the product dried overnight at room temperature. In this embodiment, the hydroxy derivative of the dye is thus obtained, as explained in Example 2.

For the purpose of this invention, the hydroxy derivative of the dye (II) may be reacted with a suitable reagent under conditions that are sufficient to form a dye phosphoramidite (I). In accordance with the embodiments of the present invention, suitable reagents may be selected from a group consisting of tetrazole, ehtylthiotetrazole, 2-cyanoethyl tetra isopropyl phosphoramidite (TIPA), and diisopropylammonium tetrazolide (DIIPT).

In one embodiment, the hydroxy derivative (II) is reacted with methylene chloride and either tetrazole (as depicted in FIG. 2) or ethylthiotetrazole under conditions that allow the formation of the phosphoramidite dye. The general structure of the phosphoramidite dye produced by this step is shown above as Formula (I).

Although different reaction conditions may be used that allow formation of phosphoramidite dye (I) of the present invention, in one embodiment discussed in more detail in Example 3, the hydroxy derivative (II) and anhydrous methylene chloride are placed in a flask protected under Argon, and stirred at 0° C. for 15 minutes. TIPA is then added to the flask using a syringe, followed by either tetrazole solution or ethylthiotetrazole (FIG. 3). The reaction is stirred at 0° C. for one hour. The mixture is then allowed to warm to room temperature, and the reaction is continued for twenty hours at room temperature. The mixture is then washed twice with 10% sodium bicarbonate solution, and the organic layer is washed twice again with distilled water. The organic phase is collected and dried with anhydrous sodium sulfate for about one hour. The sodium sulfate is filtered off, the solvent is removed under vacuum, and the mixture is dried under vacuum. The residue is dissolved in anhydrous methylene chloride and added to anhydrous ether, and then allowed to settle for about 30 minutes. The solvent is then removed and the product dried under vacuum overnight. Example 3 provides further details on suitable reaction conditions.

In another embodiment, the hydroxy derivative (II) is reacted with methylene chloride, 2-cyanoethyl tetra isopropyl phosphoramidite (TIPA), and diisopropylammonium tetrazolide (DIIPT) under conditions that allow the formation of the phosphoramidite dye, as depicted in step 3 of FIG. 3.

Although any reaction conditions may be used as long as they allow for the formation of phosphoramidite dye, in one embodiment, the hydroxy derivative (II) and anhydrous methylene chloride are placed in a flask protected under Argon, and stirred at room temperature for 15 minutes. TIPA and DIIPT are added and the mixture is stirred at room temperature for two hours under Argon or Nitrogen atmosphere. The mixture is then heated to 25-30° C. for three hours. The mixture is cooled and the reaction is allowed to continue overnight. The mixture is washed twice with sodium bicarbonate and twice with water. The organic phase is collected and dried with anhydrous sodium sulfate. The sodium sulfate is removed with a pressure funnel under Argon protection, and the residue is dried in a vacuum. The residue is dissolved in anhydrous methylene chloride, and added to anhydrous ether. The suspension is settled for 15 minutes, and the solvent is removed using a pressure funnel protected by Argon. This process is repeated, allowing a settling time of thirty minutes. The ether is filtered off, and the mixture dried under vacuum. The product is collected in a bottle, and dried overnight at room temperature under high vacuum. Example 4 provides further details on suitable reaction conditions.

Another aspect of this invention provides a method of labeling biomolecules. The method comprises the step of reacting the dye phosphoramidite of the invention having the above-described general formula (I) with the biomolecule under conditions that allow linking of the dye phosphoramidite to the biomolecule. The biomolecule may be selected from a group consisting of an amino acid, peptide, protein, nucleotide, oligonucleotide, or nucleic acid. One skilled in the art can work out the labeling conditions without undue experimentation in view of the disclosure of the present invention.

Although the phosphoramidites of the present invention may be used for labeling a broad range of biomolecules under suitable conditions, in one embodiment, discussed in more detail in Example 6, the phosphoramidite of Cyclic Cy7(OMe) was used to label an oligonucleotide. The dye phosphoramidite was dissolved in anhydrous acetonitrile, and coupled with the oligonucleotide for 10 minutes to allow bonding with the 5' end.

As discussed in more detail in Example 6, studies of the stability of labeled primers were performed and show that oligonucleotides labeled with the phosphoramidite of Cyclic-Cy7(OMe) of one embodiment of the present invention have increased functional stability over the primers labeled with the phosphoramidite of Cyclic-Cy7(H). As shown in FIG. 13, Table 4, the average half life of oligonucleotides labeled with the phosphoramidite of Cyclic-Cy7 (OMe) is 3.7 weeks, while the average half life of oligonucleotides labeled with the phosphoramidite of Cyclic-Cy7 (H) is 1.3 weeks. Similar trends are demonstrated by the PCR product yield (FIG. 15) and dye ratio (FIG. 14) data. These results show that the phosphoramidites of the present invention are superior to the prior art in their ability to effectively label oligonucleotides.

Those skilled in the art will appreciate that the phosphoramidites of dyes of the present invention can be introduced anywhere in an oligonucleotide sequence. The preferred point of addition, however, is the 5'-end of the oligonucleotide, where interference with hybridization by the dye label is minimized. Addition of a second dye is possible by using commercially available linkers to provide a multi-color labeled oligonucleotide. This invention provides, therefore, stable and convenient labels for fluorescent detection of biomolecules. The labels can be added to an oligonucleotide in a single automated step on any DNA synthesizer and do not require previously used protection-de-protection steps.

The oligonucleotides labeled with phosphoramidites of dyes of the present invention may be used as fluorescent hybridization probes to identify the presence and quantity of specific complementary nucleotide sequences in samples containing DNA or RNA. Detailed descriptions of these and many other possible applications of cyanine dye labels are provided in the pending U.S. Pat. No. 6,110,630, entitled "Efficient Activated Cyanine Dyes," U.S. Pat. No. 5,627,027, entitled "Cyanine Dyes as Labeling Reagents for Detection of Biological and Other Materials by Luminescence Methods," U.S. Pat. No. 5,569,587, entitled "Method for Labeling and Detecting Materials Employing Luminescent Arylsulfonate Cyanine Dyes," the relevant contents of which are incorporated herein by reference.

Although different reaction conditions may be used for labeling biomolecules other than oligonucleotides as explained above, in one embodiment, peptides and proteins are labeled under anhydrous conditions. Such labeled peptides and proteins are also expected to have an increased stability as compared to peptides and proteins labeled with phosphoramidites of prior art.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

The general analytical methods and characterization techniques used in these examples are identified below. $^1$H NMR spectra were recorded on a (Bruker) spectrometer at 300 MHz. Chemical shifts were recorded in parts per million ($\delta$) relative to TMS. $^{31}$P NMR spectra were recorded on a (Bruker) spectrometer at 300 MHz. Chemical shifts were recorded in parts per million ($\delta$) relative to phosphoric acid. Analytical reverse phase HPLC analyses were performed on a high pressure liquid chromatography Beckman instrument fitted with a C18 ultrasphere column (5µ particles,). 46 MM×25 CM (Beckman Cat. #235329).

EXAMPLE 1

Synthesis of Cyclic-Cy7(Cl)—OH

Figure 5:
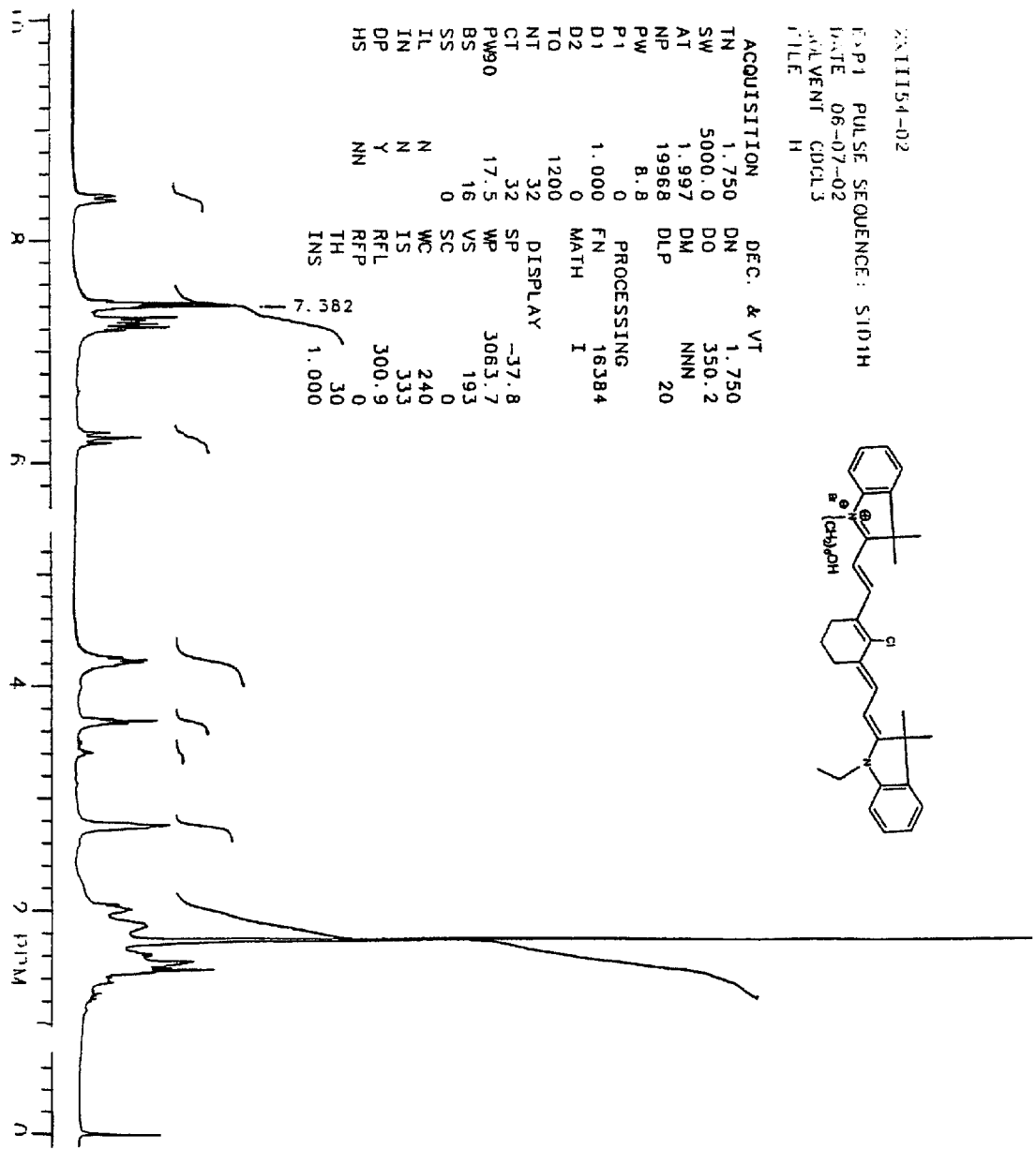
FIG. 5 depicts ³¹P NMR spectra of the hydroxy derivative of cyclic (Cl)-Cy7.

In an oven dried 500 mL round bottom flask with a magnetic stir bar and a condenser, 10.28 g of 1-(1'-hydroxyhexyl)-2,3,3-trimethylindolium bromide (30.2 mmol), 9.52 g of ethyl-2,3,3-trimethylindolium iodide (30.2 mmol), and 160 mL of anhydrous ethanol were added. All solid was dissolved by stirring the mixture at room temperature. 10.86 g of N-[(3-anilinomethylene)-2-chloro-1-cyclohexeneyl methylene]aniline monohydrochloride (linker) (30.2 mmol) were then added into the flask. The mixture was stirred at room temperature and all solid in the solution was dissolved. 6 g of sodium acetate anhydrous was then added to the flask. The solution was heated to reflux in an oil bath of 110-120° C. for 1 hour, then cooled to room temperature. The mixture was checked by Thin Layer Chromatography (TLC) (solvent system 85:5:5:5=$CH_2Cl_2$:methanol:acetone:ethyl acetate) to see if the reaction was finished. The solvent was removed under vacuum, and the mixture dried under vacuum for 2 hours. The resulting mixture was then dissolved in 30 mL of $CH_2Cl_2$, and precipitated in 300 mL of ether. The solvent was removed by filtration and all solid was collected and dried under vacuum for 1 hour. The remaining solid was then dissolved in 40 mL of $CH_2Cl_2$, and was loaded into a silica gel column. The column was eluted with a gradient solvent system (Methylene chloride: Acetonitrile: acetone, the ratio changed from 100:0:0 to 60:20:20 by volume), starting with 100% methylene chloride (about 2 L), gradually changing the solvent system as prepared. When the fraction turned green, it was collected at in segments of about 250 mL per fraction and monitored by Thin Layer Chromatography (TLC) (solvent system 85:5:5:5=$CH_2Cl_2$:methanol:acetone: ethyl acetate). The fractions containing the product were pooled into a round bottom flask and the solvent was evaporated. The product was then dried under high vacuum overnight at room temperature. The result was 9.0 g product, for a yield of 47% of Cyclic-Cy7(Cl)—OH. The following physical properties were observed:

$^1$H NMR (CDCl$_3$): $\delta$1.46 (t, 3H-CH2CH3), $\delta$1.6 (m, 4H, 2CH2) $\delta$1.8 (s, 12H, (CH3)$_4$), $\delta$1.85 (m, 4H, 2CH2), $\delta$2.0 (m, 2H, CH2 of the ring), $\delta$2.8 (t, 4H, (CH2)$_2$ of the ring), $\delta$3.75 (t, 2H, CH2), $\delta$4.2 (m, 4H, (CH2-N)$_2$), $\delta$6.2 (t, 2H), $\delta$7.2-7.55 (m, 8H, aromatic), and $\delta$8.4 (d, 2H). (FIG. 5). VIS-NIR $\lambda_{max}$ 778 nm.

EXAMPLE 2

Synthesis of Cyclic-Cy7(OMe)—OH

To an oven dried 250 mL round bottom flask with a magnetic stir bar and a condenser, purged and protected under Argon, were added 5 g of NaOMe powder and 200 mL of methanol anhydrous. The solution was stirred to make sure the NaOMe had dissolved completely. To this was added 10 g Cyclic-Cy7(Cl)—OH (15.08 mmol). The resulting mixture was heated to reflux in an oil bath of 80-100° C. for 1 hour, then cooled to room temperature. The solvent was evaporated under vacuum, and the residue dried under vacuum. The dry solid was then dissolved in 20-30 mL methylene chloride. The sample was loaded into a silica gel column. The column was eluted starting with 100% methylene chloride, gradually changing along a gradient from 1% methanol to 5% methanol. The fraction was checked by using Thin Layer Chromatography (TLC) (solvent system 85:5:5:5=$CH_2Cl_2$:methanol:acetone:ethyl acetate), and the expected fraction was collected in a 250 mL flask. The expected fraction was then pooled and all the solvent was evaporated under the vacuum. Dry the product under vacuum overnight at room temperature. The result was 8.1 g product, giving a yield of 81% of Cyclic-Cy7(OMe)—OH. The following physical properties were observed:

$^1$H NMR (CDCl$_3$): $\delta$1.45 (t, 3H, CH2-CH3), $\delta$1.55 (m, 2CH2), $\delta$1.63 (s, 12H, (CH3)$_4$), $\delta$1.8-1.9 (m, 6H, 3-CH2), $\delta$2.5 (t, 4H, 2CH2 of the ring), $\delta$3.75 (t, 2H, CH2), $\delta$3.92 (s, 3H, O-CH3), $\delta$4.2 (m, 4H, (CH2-N)2), $\delta$6.1 (dd, 2H), $\delta$7.2-7.55 (m, 8H, aromatic), and $\delta$8.0(d, 2H). (FIG. 5) VIS-NIR $\lambda_{max}$ 750 nm.

EXAMPLE 3

Synthesis of Cyclic-Cy7(OMe)-Phosphoramidite (Method 1)

To an oven dried 250 mL round bottom flask with a magnetic stir bar, purged and protected under Argon, was added 5 g of Cyclic-Cy7(OMe)-OH (7.58 mmol) and 200 mL of anhydrous methylene chloride. The solution was stirred at 0° C. (the temperature was controlled with an ice bath) for 15 min. 4.57 g of TIPA (0.015 mole) was then added into the flask by use of a syringe, followed by the addition of 15.2 mL of either 0.5 M tetrazole solution or 24.6 gm of 4% ethylthiotetrazole. The reaction mixture was stirred at 0° C. for 1 hour. The mixture was then warmed to room temperature in order to continue the reaction for about 20 hours (overnight) at room temperature. The reaction mixture was checked by TLC (solvent system 85:5:5: 5=CH$_2$Cl$_2$:methanol:acetone:ethyl acetate) to ensure that the product had a higher RF than the starting material. The reaction mixture was then transferred to a separatory funnel where it was washed twice with 200 mL of 10% sodium bicarbonate solution. The organic layer was then two times with 300 mL of distilled water, and the organic phase was collected. The organic solution was then dried with 20 g of anhydrous sodium sulfate for about 1 hour, after which the sodium sulfate was filtered off. The remaining solvent was then removed by Roto-vap under vacuum, and the residue dried under vacuum for 1 hour. The residue was dissolved in a minimal amount of anhydrous methylene chloride (around 10-20 mL) and this solution was added to 500 mL of anhydrous ether. The mixture was allowed to settle for about 30 min, before the ether was removed by means of a pressure funnel protected by Argon. The remaining solid was dried under vacuum for 30 minutes, and the above precipitating procedure was repeated once. The final product was then dried under vacuum overnight at room temperature. 3.6 g of the product Cyclic-Cy7(OMe)-Phosphoramidite was recovered, for a yield of 55%.

EXAMPLE 4

Synthesis of OMe-cyclic-Cy7-Phostphoramidite (Method 2)

Figure 6:
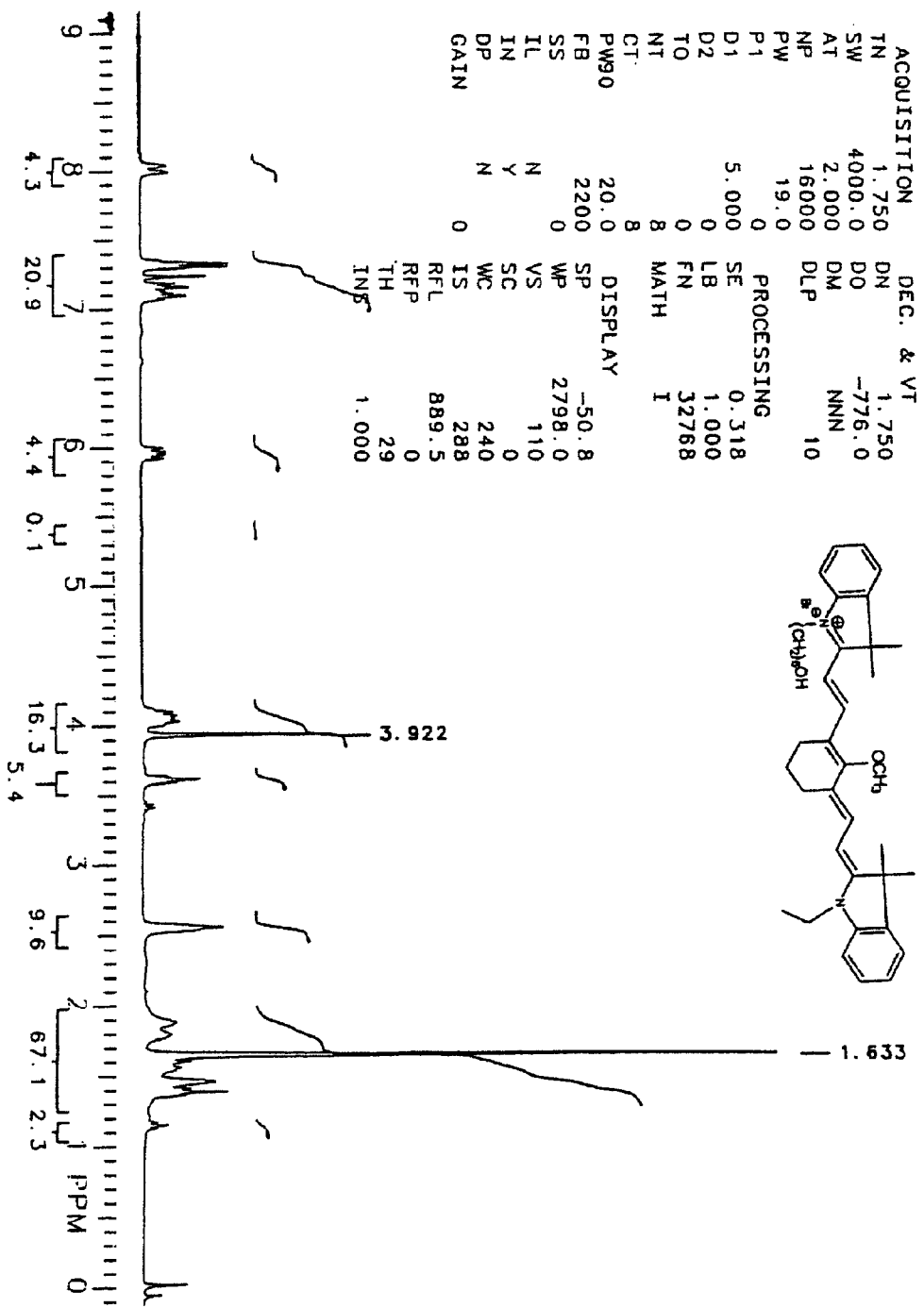
FIG. 6 depicts ³¹P NMR spectra of the hydroxy derivative of the cyclic (OCH₃)-Cy7.
Figure 7:
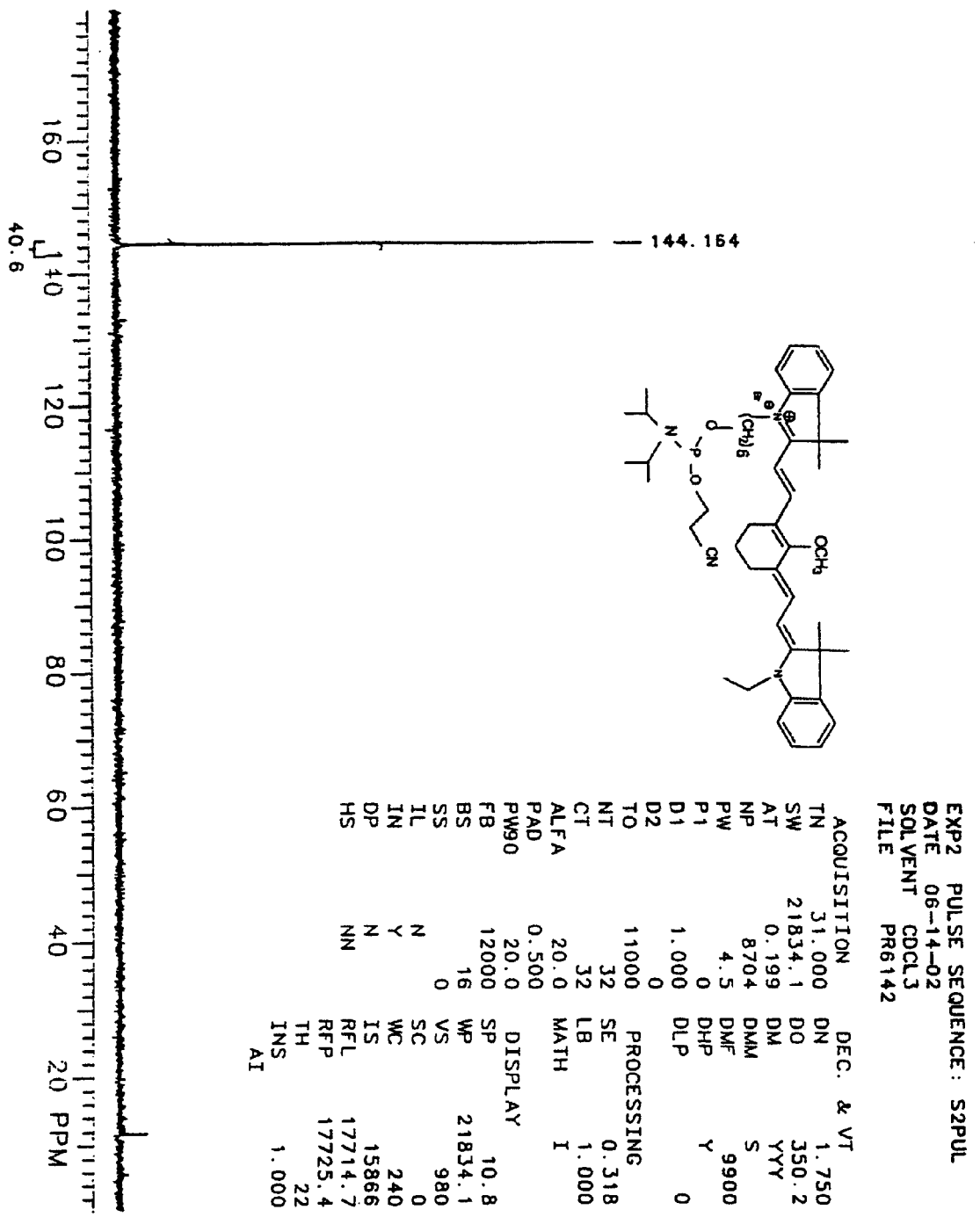
FIG. 7 depicts ³¹P NMR spectra of the cyclic (OCH₃)-Cy7 phosphoramidite.
Figure 8:
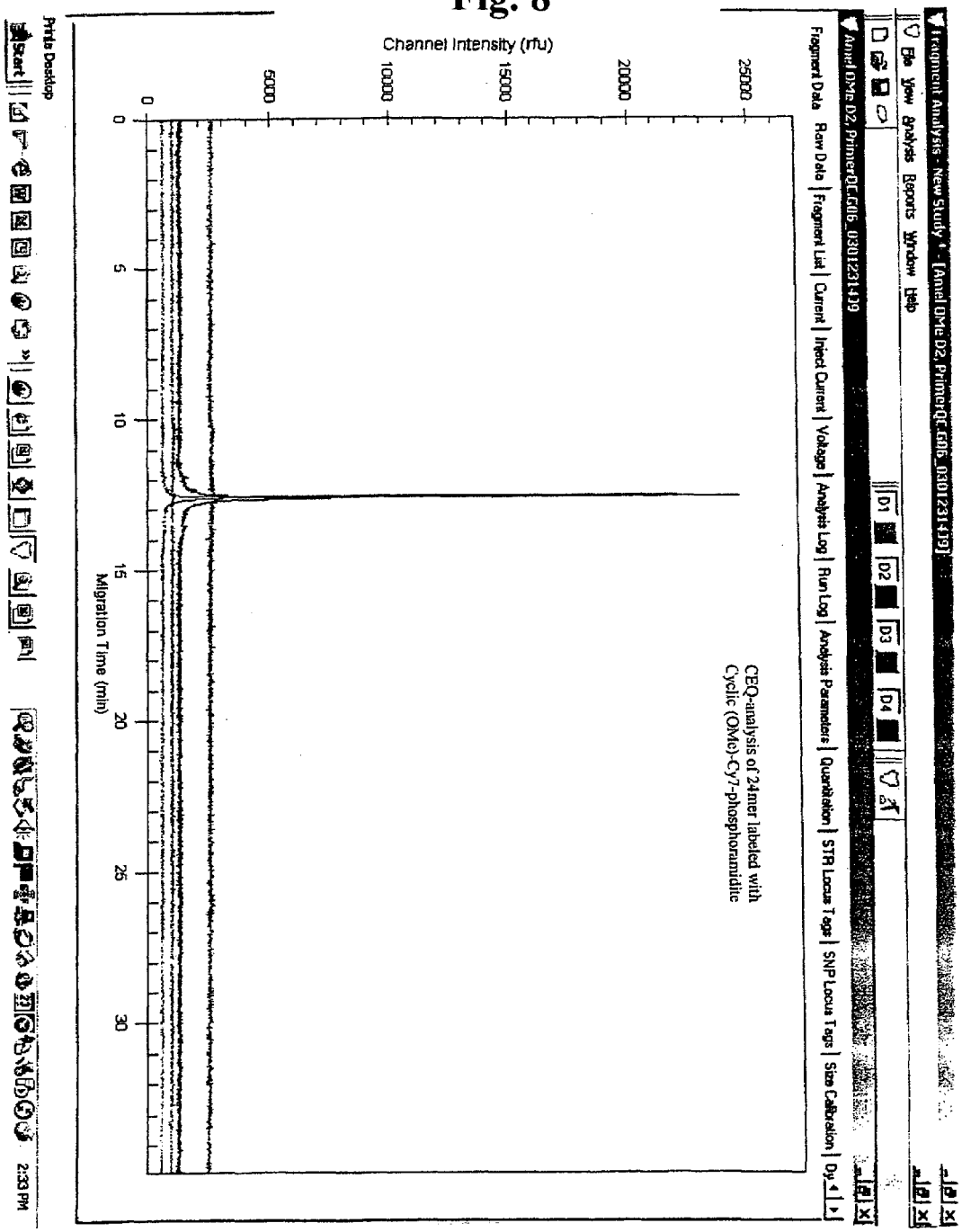
FIG. 8 depicts CEQ-analysis of a 24-mer labeled with the cyclic (OCH₃)-Cy7 phosphoramidite. CEQ is a fully automated genetic analysis system. This system automatically fills the capillary array with a linear polyacrylamide gel, denatures and loads the sample, applies the voltage program, and analyzes the data. CEQ typically analyzes DNA fragments based on size.
Figure 11:
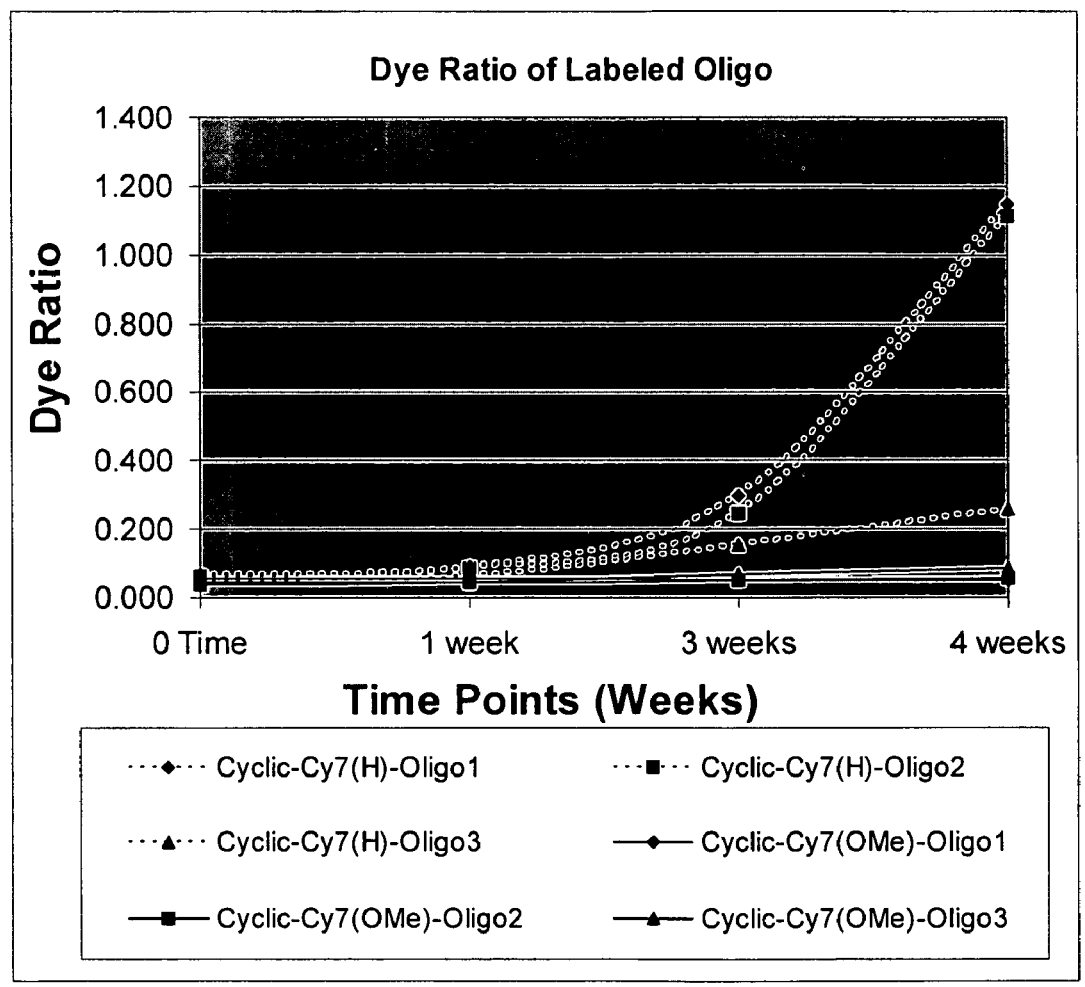
FIG. 11 shows a chart which depicts the dye ratio of labeled oligos as a function of time. Oligonucleotides 1-3 were labeled with phosphoramidites of cyclic bridged Cy7 dyes, which have either substituted (Cyclic-Cy7(OMe)) or unsubstituted (Cyclic-Cy7(H)) cyclic groups. The Dye ratio is calculated as the absorbance at 260 nm divided by the absorbance at the dye maximum (750 nm for Cyclic-Cy7(H) and 763 nm for Cyclic-Cy7(OMe)), divided by the length of the oligonucleotide.
Figure 12:
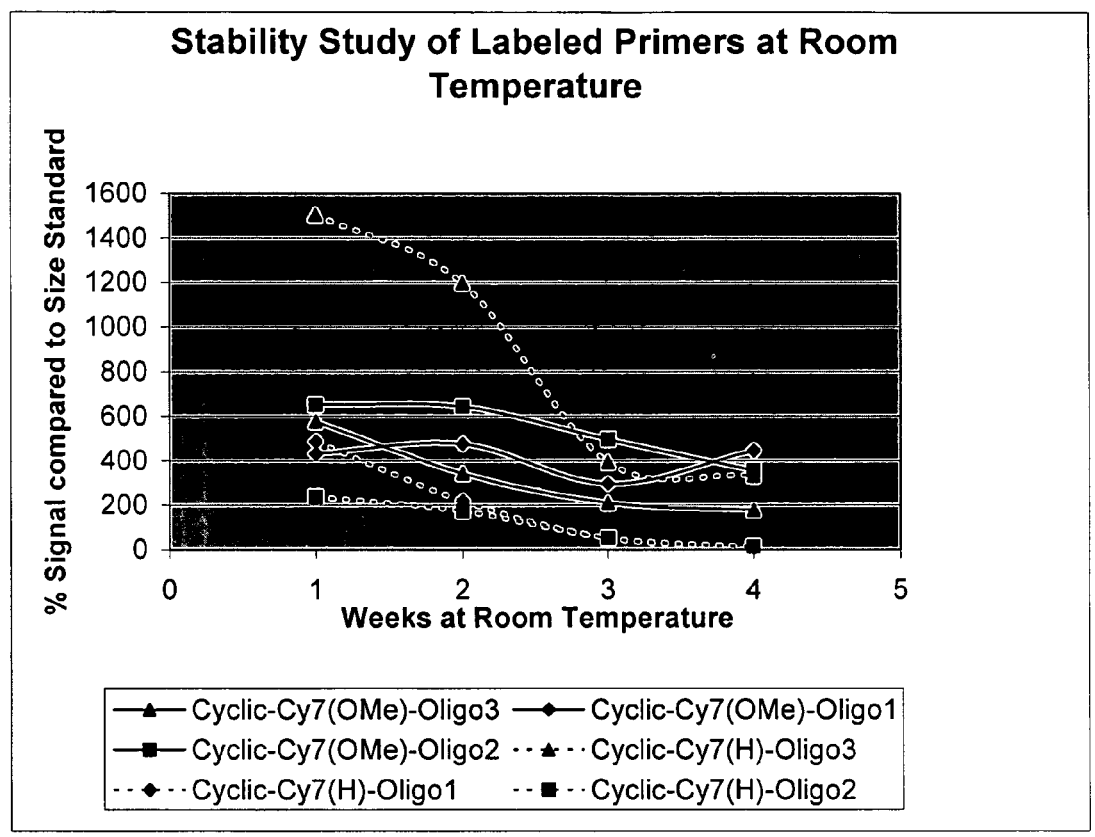
FIG. 12 shows a chart which depicts the stability of primers 1-3 as a function of time measured by CEQ as percent signal compared to size standard, which is calculated as a ratio of average allele peak heights to average size standard peak heights. Oligonucleotides 1-3 are labeled with phosphoramidites of cyclic bridged Cy7 dyes, which have either substituted or unsubstituted cyclic groups.

To an oven dried 250 mL round bottom flask with a magnetic stir bar, purged and protected under Argon, were added 5 g of Cyclic-Cy7(OMe)-OH (7.58 mmol) and 200 mL of anhydrous methylene chloride. The solution was stirred at room temperature for 15 minutes. Using a syringe, 6±0.4 g of TIPA (6.0±0.2 mL, or 0.015 mole) was added to the flask followed by 1.5 g of diisopropylammonium tetrazolide (DIIPT, activator). The reaction mixture was then stirred at room temperature for 2 hours under Argon or Nitrogen atmosphere, after which it was heated to 25-30° C. for 3 hours. The mixture was then allowed to cool to room temperature and the reaction was continued for about 16 hours (overnight) at room temperature. The reaction mixture was checked by Thin Layer Chromatography (TLC) (solvent system 85:5:5:5=CH$_2$Cl$_2$:methanol:acetone:ethyl acetate) to ensure that the product had a higher RF than the starting material. The reaction mixture was transferred to a separatory funnel and washed with 200 mL of 10% sodium bicarbonate solution twice. The organic layer was washed two times with 300 mL of distilled water. The organic phase was collected and dried with 40 g of anhydrous sodium sulfate for about 1 hour. The sodium sulfate was filtered off by use of a pressure funnel protected by Argon and the solvent was removed from the filtrate by a rotary evaporator. The residue was dried under high vacuum for 1 hour, after which the residue was dissolved in a minimal amount of anhydrous methylene chloride (about 20-30 mL). This solution was then added drop by drop to 500 mL of anhydrous ether and the suspension was allowed to settle for 15 minutes. The solvent was removed by use of a pressure funnel protected by Argon, and the remaining mixture was dried under vacuum for 1 hour. The above precipitation procedure was then repeated once, allowing the mixture settle for about 30 min. The anhydrous ether was then filtered off using pressure filter protected with Argon. The remaining solid was then dried under vacuum for 1 hour. The product was collected in a bottle, and the product was dried under high vacuum overnight at room temperature. The process gave 4.6 g of product, for a yield of 70% of OMe-cyclic-Cy7-Phosphoramidite. The following physical properties were observed:

P$^{31}$ NMR (CDCl$_3$): δ144.24 (purity 95%). (FIG. 6)

EXAMPLE 5

Accelerated Stability Study of Cyclic-Cy7(OMe) vs. Cyclic-Cy7(H)

The accelerated stability study of Cyclic-Cy7(OMe) vs. Cyclic-Cy7(H) phosphoramidite was performed at 37° C. and at room temperature. The samples were stored at 37° C. or at room temperature and at different time points phosphorous NMR, High Pressure Liquid Chromatography (HPLC) on C1 column, and coupling to an oligonucleotide was performed. The oligonucleotide was cleaved and deprotected using mild cleavage and deprotection reagent, 0.05M K$_2$CO$_3$/MeOH, evaporated and analyzed by UV-VIS spectra and % area on C-18 HPLC. The data is summarized in FIGS. 9 and 10, Tables 1-3.

The emission/absorption ratios in Tables 2 and 3 demonstrate absorbance and emission properties of the dyes at storage temperature. The ratio changes more substantially with time for Cyclic-Cy7(H) phosphoramidite as compared to Cyclic-Cy7(OMe) phosphoramidite, which indicates higher stability of Cyclic-Cy7(OMe). Similarly, the smaller decrease in the % of 31P NMR value, which is associated with dye's degradation, in case of Cyclic-Cy7(OMe) phosphoramidite demonstrates its higher stability over Cyclic-Cy7(OMe).

EXAMPLE 6

Coupling of Dye Phosphoramidite to Oligonucleotides

An accelerated stability study of labeled primers was performed at 37° C. and at room temperature. The oligonucleotides were synthesized on ABI 394 using A$^{pac}$, G$^{ipr-pac}$, C$^{ac}$ and T phosphoramidite. 100 mg of Cyclic-Cy7 (OMe) or Cyclic-Cy7(H) phosphoramidite was dissolved in 1 mL of anhydrous acetonitrile (AcCN) and coupled at 5' end of the sequence for 10 minutes. The oligonucleotide was cleaved and deprotected using 0.05M K$_2$CO$_3$/MeOH, overnight at room temperature, evaporated, and purified on reverse phase High Pressure Liquid Chromatography (HPLC). The purified oligonucleotides were stored at 37° C. and room temperature for stability study. At different time points the samples were taken out and Dye ratio and functional test was performed. The Dye Ratio is measured by Abs. 260 nm/Abs. 763 nm/Length of oligonucleotide. The Primers sequences were as follows:

```
Oligonucleotide 1:
5' GATCCCAAGCTCTTCCTCTT 3'        (SEQ ID. No: 1)

Oligonucleotide 2:
5' CCCTGGGCTCTGTAAAGAATAGTG 3'    (SEQ ID. No: 2)

Oligonucleotide 3:
5' TTCCAGCCTAGGTAGCAGTG 3'        (SEQ ID. No: 3)
```

The data associated with this study is summarized in FIGS. 11-15.

Figure 14:
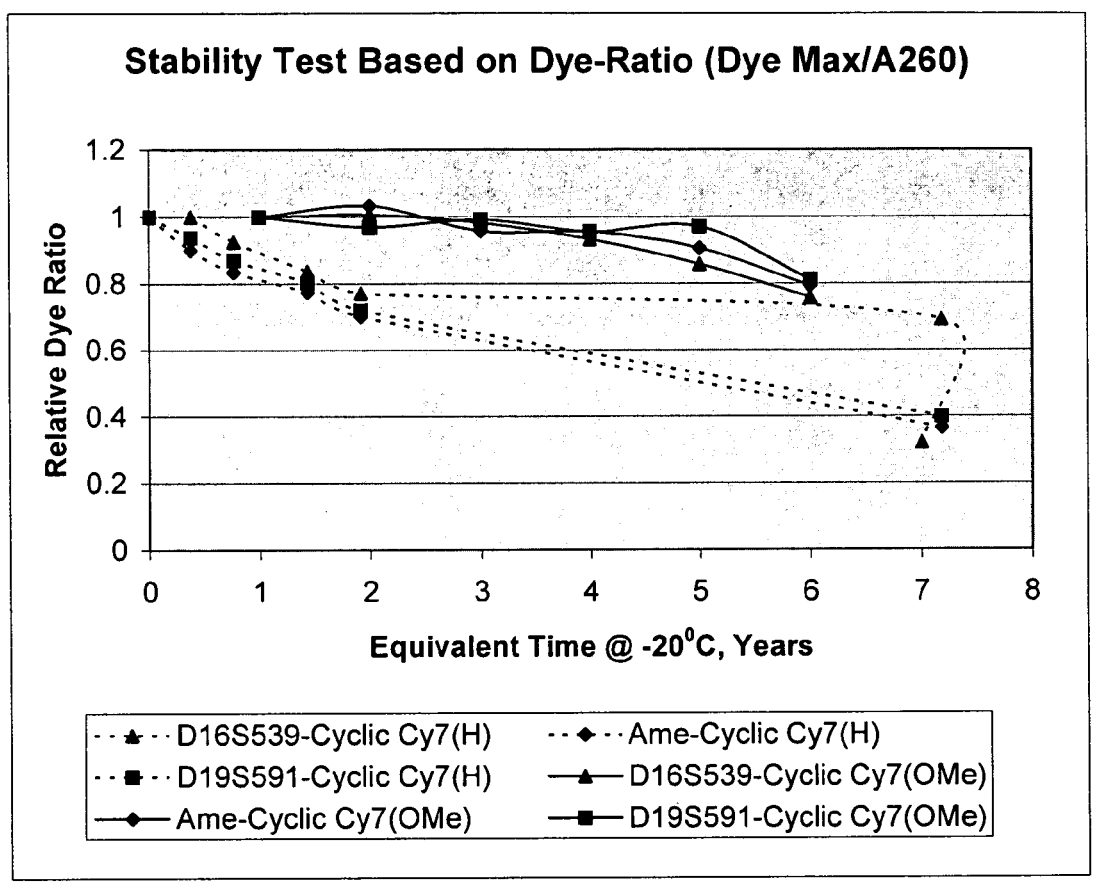
FIG. 14 shows a chart which depicts relative dye ratios as a function of equivalent time at −20° C. for D16S539 (Oligo1), Amelogenin (Oligo 2), and D19S591 (Oligo 3) labeled with phosphoramidites of cyclic bridged Cy7 dyes which had either substituted (Cy7(OMe)) or unsubstituted (Cy7(H)) cyclic groups.

Oligonucleotides labeled with the phosphoramidite of Cyclic-Cy7(OMe) show more stability over the primers labeled with the phosphoramidite of Cyclic-Cy7(H). For example, the superior stability of oligonucleotides labeled with the phosphoramidites of the present invention is demonstrated by the functional stability test (FIG. 15) and stability test based on Dye Ratio (FIG. 14). The oligonucleotides labeled with the phosphoramidites of the present invention were about 2.5 fold more stable when incubated at 37° C. for 5 days (equivalent to 7.18 years @−20° C.) The level of noise did not seem to correlate with either Cyclic-Cy7(OMe) or Cyclic Cy7(H) synthesis (FIG. 15).

What is claimed is:

1. A dye phosphoramidite having a formula (I):

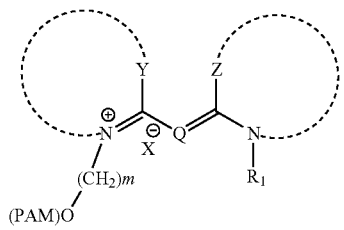

wherein:

each dotted line represents carbon atoms necessary to form a fused substituted or unsubstituted aromatic ring or rings;

m is an integer from 1 to 18;

Y and Z are independently selected from the group consisting of S, O, N, $CH_2$ and $C(CH_3)_2$;

$R_1$ is a first alkyl;

(PAM) is a phosphoramidite group;

$X^{\ominus}$ is a negative ion; and

Q is L-W, wherein L is a conjugated cyclic moiety and W is $OR_2$, wherein $R_2$ is a second alkyl.

2. The dye phosphoramidite of claim 1, wherein said aromatic ring is phenyl, naphthyl, or heterocyclic ring.

3. The dye phosphoramidite of claim 2, wherein said aromatic ring is selected from a group consisting of benzoindolinene, substituted indolinene, and substituted benzoindolinene.

4. The dye phosphoramidite of claim 1, wherein said first and second alkyls are independently selected from a group consisting of alkyls and substituted alkyls having 1 to 18 carbon atoms in their backbone.

5. The dye phosphoramidite of claim 4, wherein said first alkyl is ethyl.

6. The dye phosphoramidite of claim 4, wherein said second alkyl is methyl.

7. The dye phosphoramidite of claim 1, wherein said conjugated cyclic moiety is selected from a group consisting of cyclohexene, cyclopentene, and cycloheptene.

8. The dye phosphoramidite of claim 1, wherein said dye is a cyanine dye.

9. The dye phosphoramidite of claim 8, wherein said cyanine dye is selected from the group consisting of cyclic tricarbocyanine dye (cyclic Cy7), benzoindole cyclic cyanine dye (cyclic BCy7), and dibenzoindole cyclic cyanine dye (cyclic DBCy7).

10. The dye phosphoramidite of claim 1, wherein said negative ion is $I^\ominus$ or $Br^\ominus$.

11. The dye phosphoramidite of claim 1, wherein said phosphoramidite group is a N,N-diisopropyl-O-β-cyanoethyl phosphoramidite group.

12. A method of synthesizing a dye phosphoramidite comprising the steps of:
(a) forming a hydroxy derivative of the dye having a formula (II):

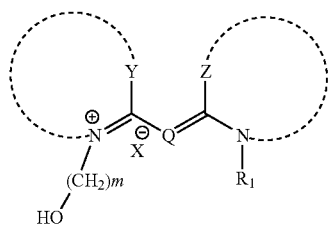

wherein each dotted line represents carbon atoms necessary to form a fused substituted or unsubstituted aromatic ring or rings;
m is an integer from 1 to 18;
Y and Z are independently selected from the group consisting of S, O, N, $CH_2$ and $C(CH_3)_2$;
$R_1$ is a first alkyl;
(PAM) is a phosphoramidite group;
$X^\ominus$ is a negative ion; and
Q is L-W, wherein L is a conjugated cyclic moiety and W is —$OR_2$, wherein $R_2$ is a second alkyl.

(b) replacing hydrogen of the OH group of the hydroxy derivative (II) with a phosphoramidite group.

13. The method of claim 12, wherein said aromatic ring is phenyl, naphthyl, or heterocyclic ring.

14. The method of claim 12, wherein said first and second alkyls are independently selected from a group consisting of alkyls and substituted alkyls having 1 to 18 carbon atoms in their backbone.

15. The method of claim 12, wherein said conjugated cyclic moiety is selected from a group consisting of cyclohexene, cyclopentene, and cycloheptene.

16. The method of claim 12, wherein said dye is a cyanine dye.

17. The method of claim 16, wherein said cyanine dye is selected from the group consisting of cyclic tricarbocyanine dye (cyclic Cy7), benzoindole cyclic cyanine dye (cyclic BCy7), and dibenzoindole cyclic cyanine dye (cyclic DBCy7).

18. The method of claim 12, wherein said phosphoramidite group is a N,N-diisopropyl-O-β-cyanoethyl phosphoramidite group.

19. The method of claim 12, wherein the step of forming the hydroxy derivative of the dye comprises reacting compounds (XI), (XII), and (XIII) under conditions that allow the formation of chlorine derivative of the dye having a general formula (XIV):

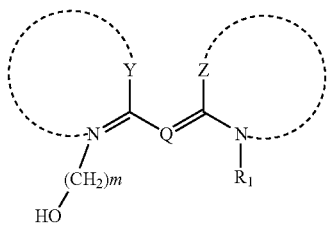

wherein Q is L-Cl, wherein L is a conjugated cyclic moiety and Cl is chlorine;
Compound (XI) having a formula:

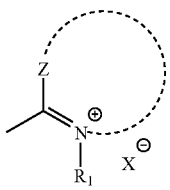

Compound (XII) having a formula:

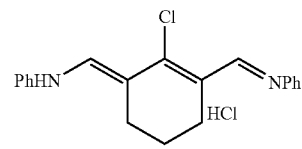

wherein Ph is phenyl; and
Compound (XIII) having a formula:

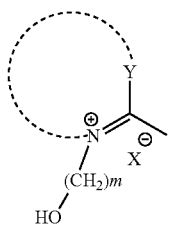

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; and $X^\ominus$ is a negative ion.

20. The method of claim 19, wherein said aromatic ring is phenyl, naphthyl, or heterocyclic ring.

21. The method of claim 19, wherein said negative ion is $Br^\ominus$ or $I^\ominus$.

22. The method of claim 19, wherein said alkyl possesses 1 to 18 carbon atoms.

23. The method of claim 22, wherein said alkyl is ethyl.

24. The method of claim 19, wherein Compound (XIII) is formed by reacting Compound (XV) with $Br(CH_2)_m$—OH under reaction conditions that allow the formation of compound (XIII), Compound (XV) having a formula:

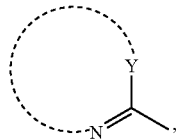

wherein dotted line represents carbon atoms necessary to form a fused substituted or unsubstituted aromatic ring; Y is selected from the group consisting of S, O, N, $CH_2$ and $C(CH_3)_2$; and m is an integer from 1 to 18.

25. The method of claim 19, wherein the dye is cyclic Cy7, Compound (XI) is 1-ethyl-2,3,3-trimethylindolinium iodide, and Compound (XIII) is 1-(1'-hydroxyhexyl)-2,3,3-trimethylindolinium bromide.

26. The method of claim 19, wherein the dye is cyclic DBCy7, Compound (XI) is 1-ethyl-1,1,2-trimethyl-H-Benz(e)indolinium iodide and Compound (XIII) is 1-(6-hydroxyhexyl)-1,1,2-trimethyl-H-Benz(e)indolinium bromide.

27. The method of claim 19, wherein the step of forming the hydroxy derivative of the dye further comprises:
replacing chlorine of the compound (XIV) with an —$OR_2$ group, wherein $R_2$ is a second alkyl.

28. The method of claim 19, wherein the step of replacing chlorine comprises heating a mixture of compound (XIV), NaOMe powder, and methanol anhydrous to reflux.

29. The method of claim 12, wherein the replacing step (b) is carried out by reacting the hydroxy derivative (II) with methylene chloride and tetrazole or ethylthiotetrazole under conditions that allow the formation of a dye phosphoramidite of formula (I):

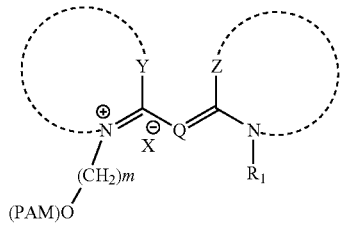

wherein:
each dotted line represents carbon atoms necessary to form a fused substituted or unsubstituted aromatic ring or rings;
m is an integer from 1 to 18;
Y and Z are independently selected from the group consisting of S, O, N, $CH_2$ and $C(CH_3)_2$;
$R_1$ is a first alkyl;
(PAM) is a phosphoramidite group;
$X^\ominus$ is a negative ion; and
Q is L-W, wherein L is a conjugated cyclic moiety and W is $OR_2$, wherein $R_2$ is a second alkyl.

30. The method of claim 12, wherein the replacing step (b) is carried out by reacting the hydroxy derivative (II) with methylene chloride, 2-cyanoethyl tetra isopropyl phosphoramidite (TIPA), and diisopropylammmonium tetrazolide (DI-IPT) under conditions that allow the formation of a dye phosphoramidite of formula (I):

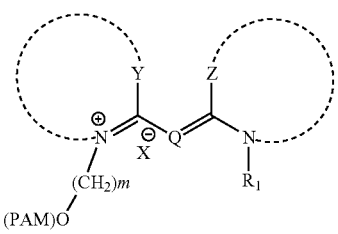

wherein:
each dotted line represents carbon atoms necessary to form a fused substituted or unsubstituted aromatic ring or rings;
m is an integer from 1 to 18;
Y and Z are independently selected from the group consisting of S, O, N, $CH_2$ and $C(CH_3)_2$;
$R_1$ is a first alkyl;
(PAM) is a phosphoramidite group;
$X^\ominus$ is a negative ion; and
Q is L-W, wherein L is a conjugated cyclic moiety and W is $OR_2$, wherein $R_2$ is a second alkyl.

31. A method of labeling a biomolecule, comprising: reacting the dye phosphoramidite having general formula (I) of claim 1 with the biomolecule under conditions that allow linking of the dye to the biomolecule.

32. The method of claim 31, wherein the biomolecule is an oligonucleotide.

33. The method of claim 31, wherein the biomolecule is a protein or a peptide.

34. A labeled oligonucleotide comprising an oligonucleotide labeled with the dye phosphoramidite having general formula (I) of claim 1.

35. A labeled protein or peptide comprising a protein or peptide labeled with the dye phosphoramidite having general formula (I) of claim 1.

36. A kit for labeling oligonucleotides comprising the dye phosphoramidite having general formula (I) of claim 1.

37. A kit for labeling proteins and polypeptides comprising the dye phosphoramidite having general formula (I) of claim 1.

* * * * *